(12) United States Patent
Moody et al.

(10) Patent No.: US 10,582,942 B2
(45) Date of Patent: Mar. 10, 2020

(54) METHODS AND DEVICES FOR SOFT TISSUE DISSECTION

(71) Applicant: PHYSCIENT, INC., Durham, NC (US)

(72) Inventors: Ryan Moody, Durham, NC (US); Hugh C. Crenshaw, Durham, NC (US); Eric T. Espenhahn, Cary, NC (US); Charles A. Pell, Durham, NC (US)

(73) Assignee: Physcient, Inc., Durham, NC (US)

( * ) Notice: Subject to any disclaimer, the term of this patent is extended or adjusted under 35 U.S.C. 154(b) by 215 days.

(21) Appl. No.: 15/304,679

(22) PCT Filed: Apr. 17, 2015

(86) PCT No.: PCT/US2015/026466
§ 371 (c)(1),
(2) Date: Oct. 17, 2016

(87) PCT Pub. No.: WO2015/161249
PCT Pub. Date: Oct. 22, 2015

(65) Prior Publication Data
US 2017/0042562 A1 Feb. 16, 2017

Related U.S. Application Data

(60) Provisional application No. 61/981,556, filed on Apr. 18, 2014.

(51) Int. Cl.
*A61B 17/32* (2006.01)
*A61B 17/00* (2006.01)

(52) U.S. Cl.
CPC .. *A61B 17/32002* (2013.01); *A61B 17/00234* (2013.01); *A61B 2017/00314* (2013.01);
(Continued)

(58) Field of Classification Search
CPC ........ A61B 17/32002; A61B 17/22004; A61B 17/320016; A61B 2017/320044;
(Continued)

(56) References Cited

U.S. PATENT DOCUMENTS

| 900,300 A | 10/1908 | Nicolas |
|---|---|---|
| 1,192,451 A | 7/1916 | Pfefferkorn |

(Continued)

FOREIGN PATENT DOCUMENTS

| CN | 101686839 A | 3/2010 |
|---|---|---|
| CN | 103648415 A | 3/2014 |

(Continued)

OTHER PUBLICATIONS

Examination Report No. 2 for Australian Patent Application No. 2013251330, dated Jun. 4, 2018, 2 pages.

(Continued)

*Primary Examiner* — Katrina M Stransky
(74) *Attorney, Agent, or Firm* — Withrow & Terranova, P.L.L.C.

(57) ABSTRACT

Methods and devices for blunt dissection include a drive mechanism comprising an elongate rotary drive train having a first proximal end connected to a mounting base for attaching to a handle or a surgical robot and a second distal end. The drive mechanism comprises a differential dissecting member (DDM) configured to be rotatably attached to the second distal end. The drive mechanism further comprises a mechanism configured to mechanically rotate the DDM about a substantially transverse axis of member rotational oscillation, thereby causing at least one tissue engaging surface to move in at least one direction against complex tissue and selectively engage the complex tissue such that when the DDM is pressed into the complex tissue, the at least one tissue engaging surface moves across the (Continued)

complex tissue and disrupts at least one soft tissue in the complex tissue, but does not disrupt firm tissue in the complex tissue.

11 Claims, 50 Drawing Sheets

(52) U.S. Cl.
CPC ............ A61B 2017/320004 (2013.01); A61B 2017/32006 (2013.01); A61B 2017/320044 (2013.01)

(58) Field of Classification Search
CPC ....... A61B 2017/320028; A61B 2017/320032; A61B 2017/32004; A61B 17/32037; A61B 17/3207; A61B 17/320758; A61B 17/320725; A61B 17/320783; A61B 17/32075
See application file for complete search history.

(56) References Cited

U.S. PATENT DOCUMENTS

| | | | |
|---|---|---|---|
| 1,506,510 A | 8/1924 | Thuau | |
| 1,945,247 A | 1/1934 | Wezel | |
| 2,547,134 A | 4/1951 | McLean | |
| 2,766,524 A | 10/1956 | Dagneau | |
| 2,972,350 A | 2/1961 | Deker | |
| 3,263,681 A | 8/1966 | Nechtow et al. | |
| 3,435,522 A | 4/1969 | Wezel et al. | |
| 3,554,197 A | 1/1971 | Dobble | |
| 3,618,611 A | 11/1971 | Urban | |
| 3,978,862 A | 9/1976 | Morrison | |
| 4,106,181 A | 8/1978 | Mattchen | |
| 4,432,117 A | 2/1984 | Iskiw | |
| 4,477,256 A | 10/1984 | Hirsch | |
| 4,490,885 A | 1/1985 | Iskiw et al. | |
| 4,572,187 A | 2/1986 | Schetrumpf | |
| 4,608,982 A | 9/1986 | Pollard | |
| 4,749,376 A | 6/1988 | Kensey et al. | |
| 4,768,504 A | 9/1988 | Ender | |
| 4,844,088 A | 7/1989 | Kambin | |
| 4,990,134 A | 2/1991 | Auth | |
| 5,201,752 A | 4/1993 | Brown et al. | |
| 5,205,816 A | 4/1993 | Dodson et al. | |
| 5,405,348 A | 4/1995 | Anspach, Jr. et al. | |
| 5,441,445 A | 8/1995 | Karubian et al. | |
| 5,445,561 A | 8/1995 | Elmer | |
| 5,456,011 A | 10/1995 | Inkster | |
| 5,522,788 A | 6/1996 | Kuzmak | |
| 5,527,331 A | 6/1996 | Kresch et al. | |
| 5,591,186 A | 1/1997 | Wurster et al. | |
| 5,658,307 A | 8/1997 | Exconde | |
| 5,707,383 A | 1/1998 | Bays et al. | |
| 5,725,479 A | 3/1998 | Knight et al. | |
| 5,779,713 A | 7/1998 | Turjanski et al. | |
| 5,817,121 A | 10/1998 | Christoudias | |
| 5,871,497 A | 2/1999 | Young | |
| 5,919,203 A | 7/1999 | Husted et al. | |
| 5,925,055 A | 7/1999 | Adrian et al. | |
| 6,001,120 A | 12/1999 | Levin | |
| 6,080,102 A | 6/2000 | Konou et al. | |
| 6,391,040 B1 | 5/2002 | Christoudias | |
| 6,423,078 B1 | 7/2002 | Bays et al. | |
| 6,869,439 B2 | 3/2005 | White et al. | |
| 7,367,981 B2 | 5/2008 | Bernaz | |
| 7,422,592 B2 | 9/2008 | Morley et al. | |
| D581,053 S | 11/2008 | Gesler, III | |
| 7,540,875 B2 | 6/2009 | Jessen | |
| 7,686,823 B2 | 3/2010 | Pingleton et al. | |
| 7,842,058 B2 | 11/2010 | Simpson et al. | |
| 8,048,100 B2 | 11/2011 | Kadykowski et al. | |
| 8,052,662 B2 | 11/2011 | Zelickson et al. | |
| 8,157,832 B2 | 4/2012 | Refai | |
| 8,372,096 B2 | 2/2013 | Kadykowski et al. | |
| 8,460,331 B2 | 6/2013 | Chin | |
| 8,636,759 B2 | 1/2014 | Pingleton et al. | |
| 9,538,995 B2 | 1/2017 | Crenshaw et al. | |
| 2003/0009166 A1 | 1/2003 | Moutafis et al. | |
| 2003/0144680 A1 | 7/2003 | Kellogg et al. | |
| 2005/0107816 A1 | 5/2005 | Pingleton et al. | |
| 2005/0209610 A1 | 9/2005 | Carrison | |
| 2006/0009796 A1 | 1/2006 | Carusillo et al. | |
| 2007/0167966 A1 | 7/2007 | Simpson et al. | |
| 2008/0119860 A1 | 5/2008 | McCarthy | |
| 2008/0306335 A1 | 12/2008 | Lau et al. | |
| 2009/0261690 A1 | 10/2009 | Mashimo et al. | |
| 2009/0312783 A1 | 12/2009 | Whayne et al. | |
| 2010/0010525 A1* | 1/2010 | Lockard ............... A61B 17/221 606/170 |
| 2010/0016853 A1 | 1/2010 | Burbank | |
| 2010/0114138 A1 | 5/2010 | Graham | |
| 2010/0222801 A1 | 9/2010 | Pingleton et al. | |
| 2010/0256662 A1 | 10/2010 | Racenet et al. | |
| 2010/0312186 A1 | 12/2010 | Suchdev et al. | |
| 2011/0034918 A1 | 2/2011 | Reschke | |
| 2012/0071909 A1 | 3/2012 | Fischvogt et al. | |
| 2012/0101489 A1 | 4/2012 | Bloom et al. | |
| 2012/0109172 A1 | 5/2012 | Schmitz et al. | |
| 2012/0191121 A1 | 7/2012 | Chen et al. | |
| 2012/0209141 A1 | 8/2012 | Peliks | |
| 2013/0310869 A1 | 11/2013 | Crenshaw et al. | |
| 2013/0331833 A1 | 12/2013 | Bloom | |
| 2014/0058394 A1 | 2/2014 | Siegal et al. | |
| 2014/0114339 A1 | 4/2014 | Pingleton et al. | |
| 2014/0364890 A1 | 12/2014 | Moody et al. | |

FOREIGN PATENT DOCUMENTS

| | | |
|---|---|---|
| EP | 1882538 A2 | 1/2008 |
| EP | 2777523 A1 | 9/2014 |
| GB | 1457544 A | 12/1976 |
| WO | 0149194 A2 | 7/2001 |
| WO | 2006017066 A2 | 2/2006 |
| WO | 2007100914 A2 | 9/2007 |
| WO | 2008022257 A2 | 2/2008 |
| WO | 2008127887 A1 | 10/2008 |

OTHER PUBLICATIONS

Notice of Acceptance for Australian Patent Application No. 2013251330, dated Jul. 2, 2018, 3 pages.
Examination Report No. 1 for Australian Patent Application No. 2014342631, dated Jul. 27, 2018, 3 pages.
Notice of Rejection for Japanese Patent Application No. 2016-526849, dated Jul. 31, 2018, 12 pages.
Extended European Search Report for European Patent Application No. 14857187.0, dated Jun. 12, 2017, 8 pages.
First Examination Report for New Zealand Patent Application No. 725053, dated May 3, 2017, 5 pages.
Non-Final Office Action for U.S. Appl. No. 15/304,720, dated Dec. 10, 2018, 13 pages.
Second Office Action for Chinese Patent Application No. 201480071443.8, dated Oct. 12, 2018, 12 pages.
First Office Action for Chinese Patent Application No. 201480071443.8, dated Nov. 29, 2017, 27 pages.
Extended European Search Report for European Patent Application No. 17180994.0, dated Dec. 6, 2017, 8 pages.
Examiner's Decision of Rejection for Japanese Patent Application No. 2015-509216, dated Dec. 19, 2017, 8 pages.
Further Examination Report for New Zealand Patent Application No. 725053, dated Jan. 8, 2018, 2 pages.
Second Office Action and Search Report for Chinese Patent Application No. 201380034142.3, dated Feb. 15, 2017, 21 pages.
Notice of Rejection for Japanese Patent Application No. 2015-509216, dated Feb. 28, 2017, 18 pages.
Supplementary Examination Report for Singapore Patent Application No. 11201406985P, dated Jan. 19, 2017, 2 pages.

(56) References Cited

OTHER PUBLICATIONS

Notice of Eligibility for Grant and Supplementary Examination Report for Singapore Patent Application No. 11201603273P, dated Sep. 4, 2017, 3 pages.
Extended European Search Report for European Patent Application No. 15780427.9, dated Nov. 14, 2017, 7 pages.
Cox, III, et al., "Decreased Splatter in Dermabrasion," Archives of Facial Plastic Surgery, vol. 2, Jan.-Mar. 2000, pp. 23-26.
Non-Final Office Action for U.S. Appl. No. 13/872,766, dated Jun. 17, 2016, 34 pages.
Non-Final Office Action for U.S. Appl. No. 14/065,191, dated May 31, 2016, 23 pages.
First Office Action for Chinese Patent Application No. 201380034142.3, dated Jun. 2, 2016, 8 pages.
Extended European Search Report for European Patent Application No. 13780834.1, dated Aug. 21, 2015, 5 pages.
Examination Report for European Patent Application No. 13780834.1, dated Jul. 21, 2016, 3 pages.
First Examination Report for New Zealand Patent Application No. 701634, dated Jan. 14, 2016, 3 pages.
Further Examination Report for New Zealand Patent Application No. 701634, dated Apr. 26, 2016, 2 pages.
Further Examination Report Postponed Acceptance for New Zealand Patent Application No. 701634, dated Jul. 27, 2016, 1 page.
International Search Report and Written Opinion for International Patent Application No. PCT/US2013/038673 dated Sep. 27, 2013, 23 pages.
International Preliminary Report on Patentability for International Patent Application No. PCT/US2013/038673, dated Nov. 6, 2014, 16 pages.
International Search Report and Written Opinion for International Patent Application No. PCT/US2014/062382, dated Feb. 3, 2015, 12 pages.
International Preliminary Report on Patentability for International Patent Application No. PCT/US2014/062382, dated May 12, 2016, 9 pages.
Invitation to Pay Additional Fees and Partial International Search for International Patent Application No. PCT/US2015/026466, dated Jun. 18, 2015, 7 pages.
International Search Report and Written Opinion for International Patent Application No. PCT/US2015/026466, dated Sep. 15, 2015, 14 pages.
International Preliminary Report on Patentability for International Patent Application No. PCT/US2015/026466, dated Oct. 27, 2016, 9 pages.
International Search Report and Written Opinion for International Patent Application No. PCT/US2015/027156, dated Aug. 3, 2015, 11 pages.
International Preliminary Report on Patentability for International Patent Application No. PCT/US2015/027156, dated Nov. 3, 2016, 9 pages.
Notice of Allowance and Examiner-Initiated Interview Summary for U.S. Appl. No. 13/872,766, dated Nov. 4, 2016, 11 pages.
Notice of Allowance and Examiner-Initiated Interview Summary for U.S. Appl. No. 14/065,191, dated Jan. 10, 2017, 11 pages.
Examination Report No. 1 for Australian Patent Application No. 2013251330, dated Jun. 22, 2017, 5 pages.
Third Office Action for Chinese Patent Application No. 201380034142.3, dated Sep. 5, 2017, 4 pages.
Examination Report for European Patent Application No. 14857187.0, dated Jan. 31, 2019, 6 pages.
Final Notice of Rejection for Japanese Patent Application No. 2016-526849, dated Jan. 22, 2019, 9 pages.
Notice of Rejection for Japanese Patent Application No. 2016-563016, dated Feb. 12, 2019, 11 pages.
First Office Action for Mexican Patent Application No. MX/a/2014/013035, dated Feb. 11, 2019, 4 pages.
Non-Final Office Action for U.S. Appl. No. 15/457,169, dated Apr. 26, 2019, 26 pages.
Notice of Allowance for U.S. Appl. No. 15/304,720, dated Jun. 5, 2019, 9 pages.
Notice of Acceptance for Australian Patent Application No. 2014342631, dated Jul. 15, 2019, 3 pages.
Notice of Rejection for Japanese Patent Application No. 2018-079250, dated Jul. 30, 2019, 11 pages.
Final Office Action for U.S. Appl. No. 15/457,169, dated Sep. 20, 2019, 7 pages.
Office Action for Canadian Patent Application No. 2,871,827, dated May 3, 2019, 3 pages.
Office Action for Canadian Patent Application No. 2,871,827, dated Oct. 11, 2019, 4 pages.
Notice of Preliminary Rejection for Korean Patent Application No. 10-2014-7033376, dated Oct. 29, 2019, 7 pages.
Extended European Search Report for European Patent Application No. 19177704.4, dated Nov. 14, 2019, 8 pages.
Preliminary Office Action for Brazilian Patent Application No. 112014027081-3, dated Dec. 16, 2019, 5 pages.
Notice of Allowance for U.S. Appl. No. 15/457,169, dated Dec. 30, 2019, 10 pages.

* cited by examiner

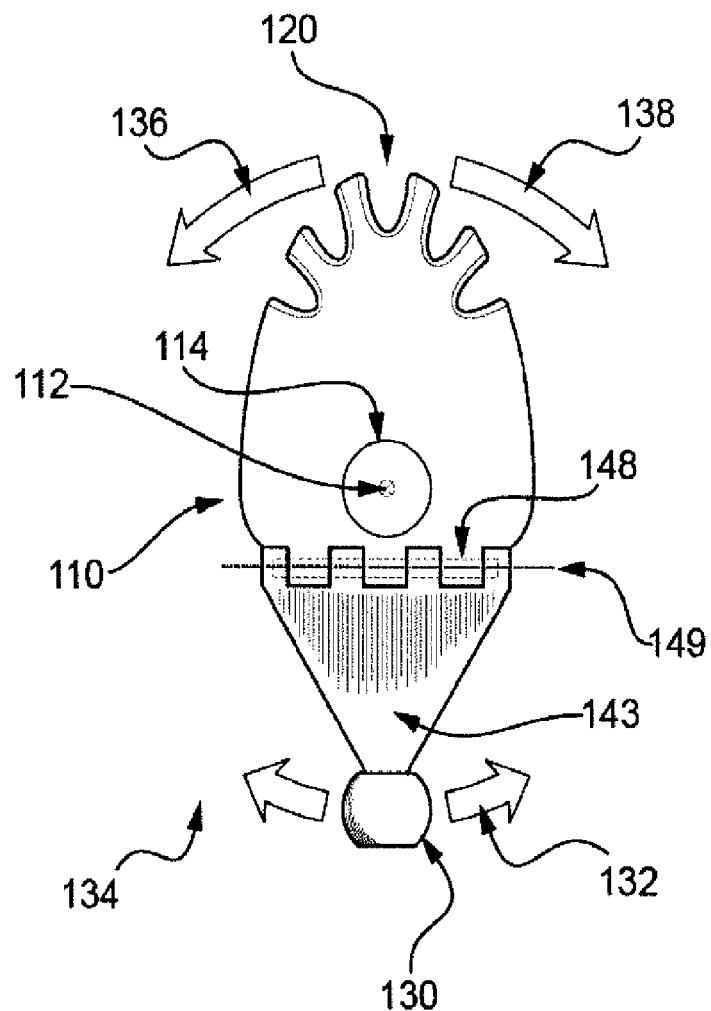

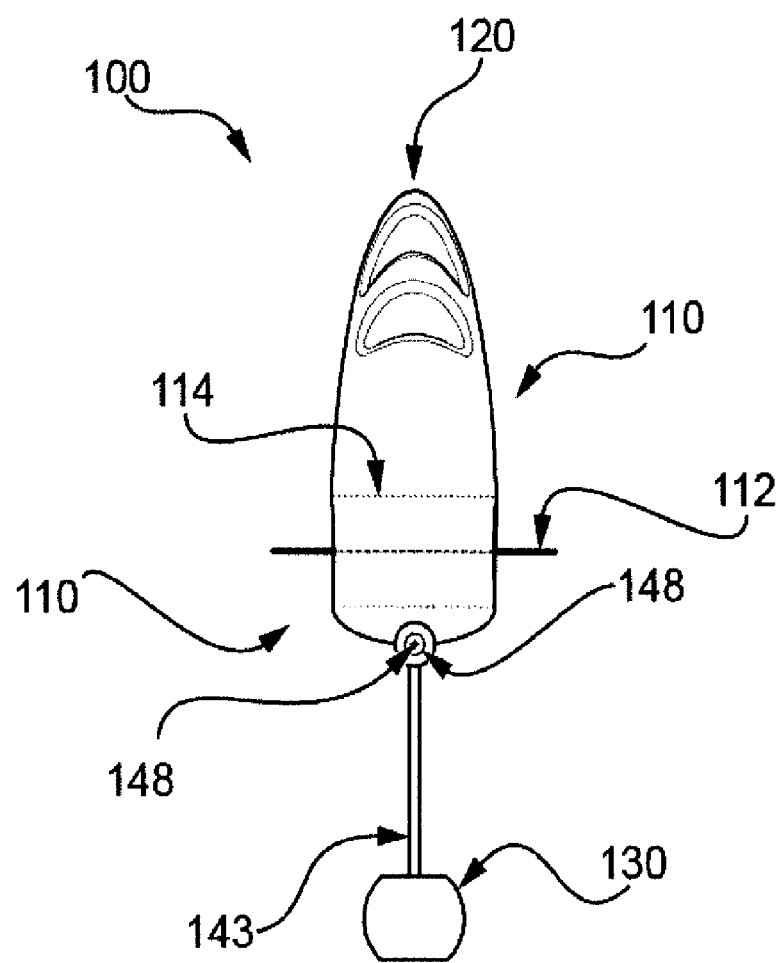

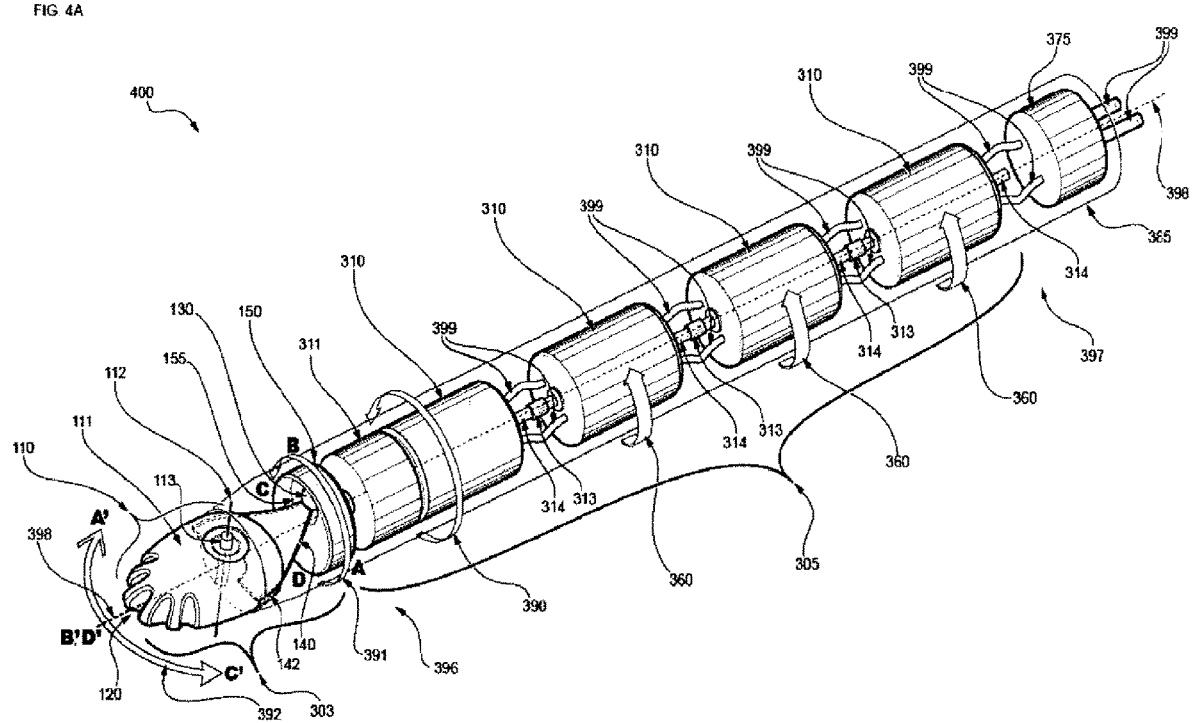

FIG. 5C-1
FIG. 5C-2
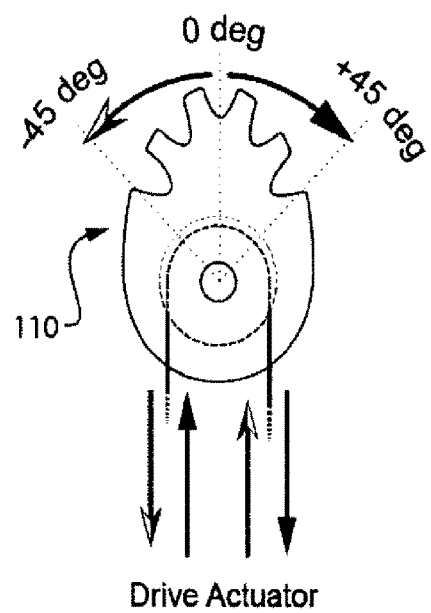
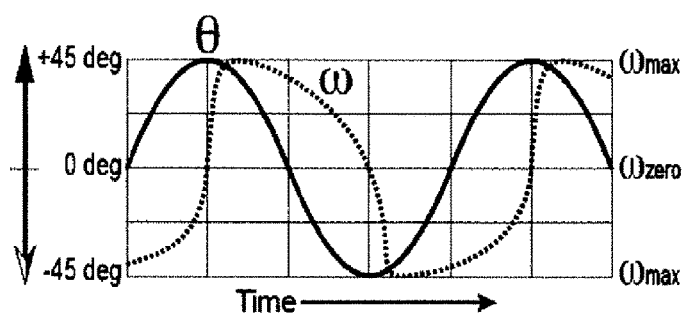

Drive Actuator

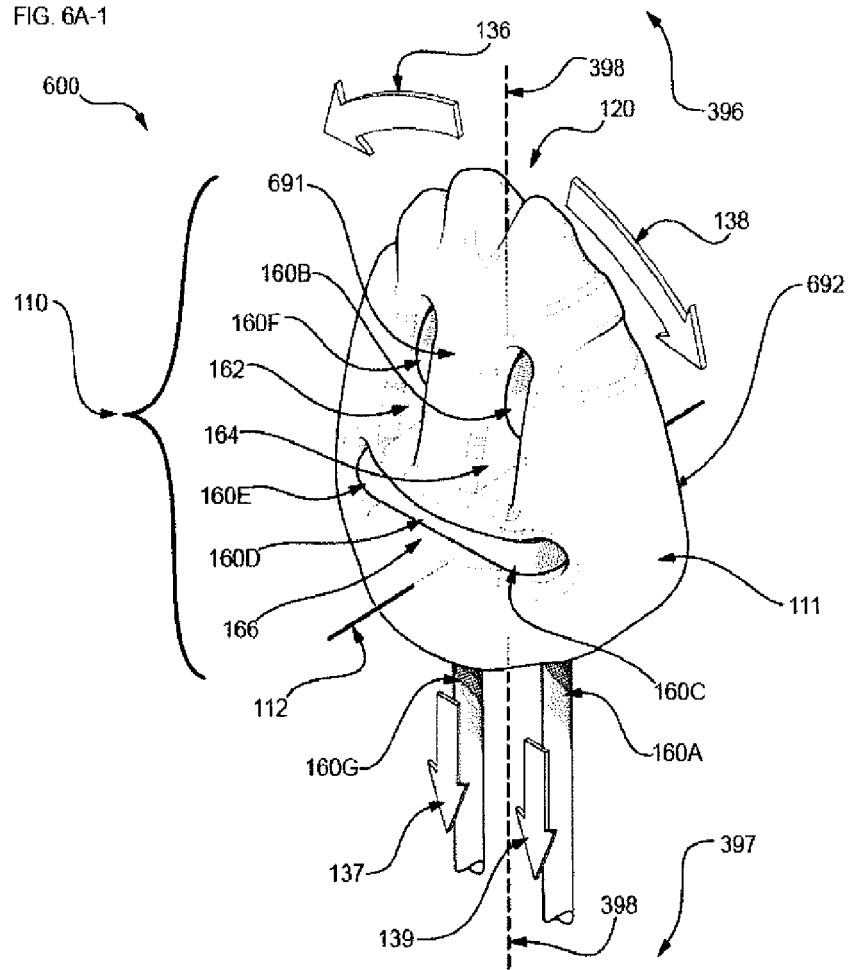

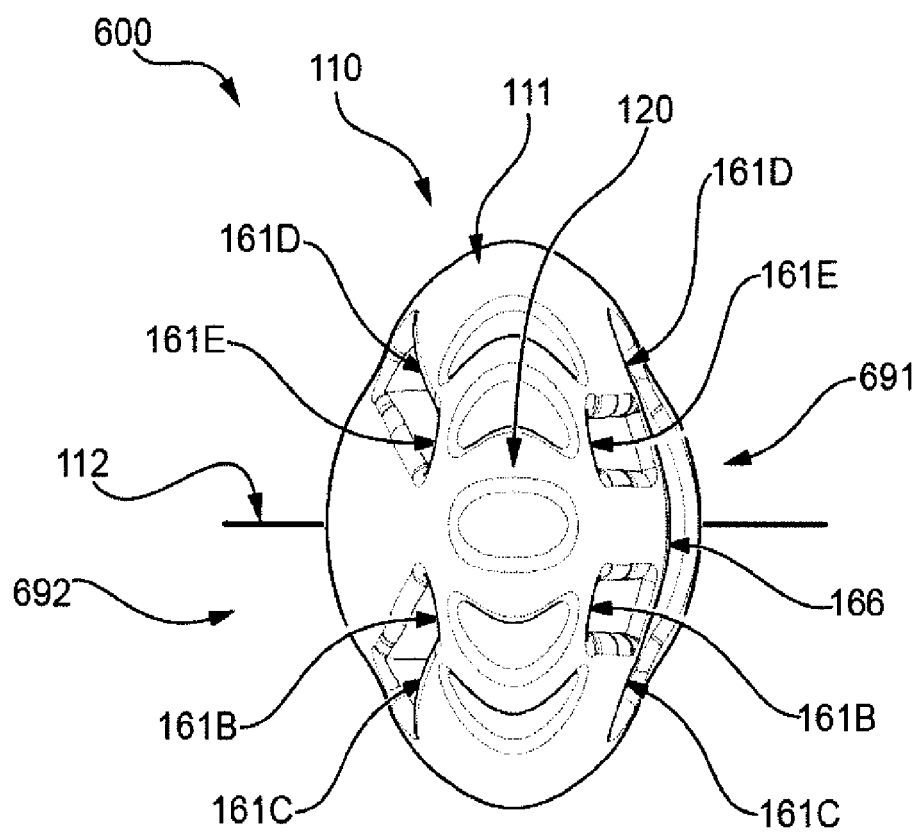

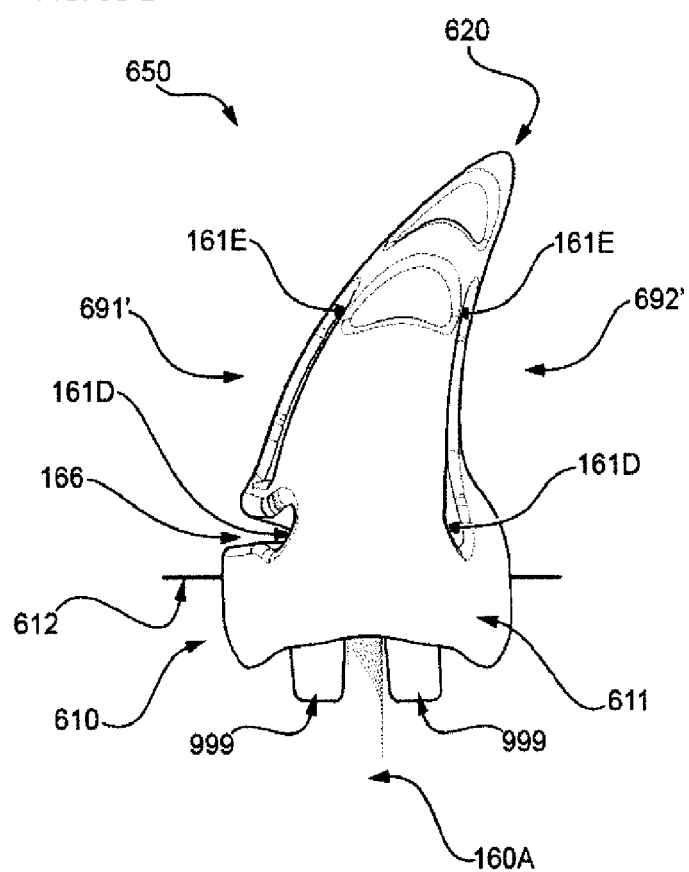

METHODS AND DEVICES FOR SOFT TISSUE DISSECTION

This application is a 35 U.S.C. § 371 national phase filing of International Application No. PCT/US2015/026466, filed Apr. 17, 2015, the disclosure of which is incorporated herein by reference in its entirety.

PRIORITY APPLICATIONS

The present application claims priority to U.S. Provisional Patent Application No. 61/981,556, entitled "Instruments, Devices, and Related Methods for Soft Tissue Dissection," filed on Apr. 18, 2014, which is incorporated herein by reference in its entirety.

The present application is also related to U.S. patent application Ser. No. 14/065,191, entitled "Instruments, Devices, and Related Methods for Soft Tissue Dissection," filed on Oct. 28, 2013, now issued as U.S. Pat. No. 9,592,069, which in turn is a continuation-in-part application of, and claims priority to, U.S. patent application Ser. No. 13/872,766 entitled "Instruments, Devices, and Related Methods for Soft Tissue Dissection", filed Apr. 29, 2013, now issued as U.S. Pat. No. 9,538,995, which in turn claims priority to the following three Provisional applications: U.S. Provisional Patent Application No. 61/783,834, entitled "Instruments, Devices, and Related Methods for Soft Tissue Dissection," filed on Mar. 14, 2013; U.S. Provisional Patent Application No. 61/744,936, entitled "Instrument for Soft Tissue Dissection," filed on Oct. 6, 2012; and U.S. Provisional Patent Application No. 61/687,587, entitled "Instrument for Soft Tissue Dissection," filed on Apr. 28, 2012, all of which are incorporated herein by reference in their entireties.

BACKGROUND

Field of the Disclosure

The field of the disclosure relates to methods or devices used to dissect tissue during surgery or other medical procedures.

Technical Background

Surgeons sever or separate patients' tissues as a major component of most surgical procedures. Called "dissection," this is how surgeons tunnel from an accessible region of a patient to reach a target within. The two dominant dissection techniques are: (1) "sharp dissection," where surgeons sever tissues with either scissors, scalpels, electrosurgical devices, and other cutting instruments; and (2) "blunt dissection," consisting of separating tissues by controlled tearing of one tissue from another.

The advantage of sharp dissection is that the cutting instrument easily cuts through any tissue. The cut itself is indiscriminate, slicing through all tissues to which the instrument is applied. This is also the disadvantage of sharp dissection, especially when trying to isolate a first tissue without damaging it, when the first tissue is embedded in, and is obscured by, a second tissue or, more commonly, is enveloped in many tissues. Accidental cutting of a blood vessel, a nerve, or of the bowel, for example, is a constant threat for even the most experienced surgeons and can rapidly lead to serious, even life-threatening, intra-operative complications, with prolonged consequences for the patient. When employing minimally invasive procedures, for example laparoscopy or the use of a surgical robot, the chances of surgical error increase.

Isolation of a first tissue embedded in other tissues is thus frequently performed by blunt dissection. In blunt dissection, a blunt instrument is used to force through a tissue, to force apart two tissues, or to otherwise separate tissues by tearing rather than cutting. Almost all surgeries require blunt dissection of tissues to expose target structures, such as blood vessels to be ligated, or nerve bundles to be avoided. Examples in thoracic surgery include isolation of blood vessels during hilar dissection for lobectomy and exposure of lymph nodes.

Blunt dissection includes a range of maneuvers, including various ways to tease apart or tear soft tissues, such as the insertion of blunt probes or instruments, inverted action (i.e., spreading) of forceps, and pulling of tissues with forceps or by rubbing with a "swab dissector" (e.g., surgical gauze held in a forceps, or a purpose-built, disposable swab stick). When needed, sharp dissection is used judiciously to cut tissues that resist tearing during blunt dissection.

The general goal of blunt dissection is to tear or otherwise disrupt occluding tissue, such as membranes and mesenteries, away from the target structure without tearing or disrupting either the target structure or critical structures such as nearby vessels or nerves. The surgeon capitalizes on the different mechanical behaviors of tissues, such as the different stiffness of adjacent tissues, or the existence of planes of softer tissue between firmer tissues. Frequently, the surgeon's goal is to isolate a target tissue that is mechanically firm, being composed of more tightly packed fibrous components, and is embedded in a tissue that is mechanically soft, being composed of more loosely packed fibrous components (for example, loose networks of collagen, reticulin, or elastin). More tightly packed fibrous tissues include tissues composed of tightly packed collagen and other fibrous connective tissues, usually having highly organized anisotropic distributions of fibrous components, often with hierarchical composition. Examples include blood vessels, nerve sheaths, muscles, fascia, bladders, and tendons. More loosely packed fibrous tissues have a much lower number of fibers per unit volume or are composed of less well organized materials such as fat and mesenteries. Fibrous components include fibers, fibrils, filaments, and other filamentous components. When a tissue is referred to as "fibrous", the reference is typically to extracellular filamentous components, such as collagen and elastin—proteins that polymerize into linear structures of varying and diverse complexity to form the extracellular matrix. As mentioned in the previous paragraph, the density, orientation, and organization of fibrous components greatly determine the tissue's mechanical behavior. Sometimes, tissues are referred to as "tough, fibrous tissues" indicating that the fibrous or filamentous components are densely packed, organized, and comprise a significant fraction of the bulk of the tissue. However, all tissues are fibrous, to one extent or another, with fibers and other filamentous extracellular components being present in virtually every tissue.

What is important to the present discussion is that softer tissues tear more easily than firmer tissues, so blunt dissection attempts to proceed by exerting sufficient force to tear softer tissue but not firmer tissue.

Blunt dissection can be difficult and is often time-consuming. Judging the force to tear a soft tissue, but not a closely apposed firm tissue, is not easy. Thus, blood vessels can be torn, Nerves can be stretched or torn. In response, surgeons attempt judicious sharp dissection, but blood vessels, nerves, and airways can be cut, especially the smaller side branches, which become exponentially more common at smaller scales. This all leads to long, tedious dissections and increased risk of complications, like bleeding, air leaks from the lungs, and nerve damage.

Surgeons frequently use forceps for blunt dissection. FIGS. 1A and 1B show a typical forceps 10 of the prior art. FIG. 1A shows the forceps 10 in the closed position for clamping a tissue 34 between the opposing first clamp element 30 and second clamp element 31. FIG. 1B shows the forceps 10 in the open position, forcing tissue 34 apart. A first finger engager 20 and an opposing second finger engager 21 are used to actuate the mechanism. First finger engager 20 drives first clamp element 30, and second finger engager 21 drives second clamp element 31. A pivot 40 attaches the first clamp element 30 and the second clamp element 31, permitting a scissor-like action to force the first clamp element 30 and the second clamp element 31 together or apart, thereby clamping tissue 34 between the two clamp surfaces 35 and 36, or rending tissue 34 by the spreading of the first clamp element 30 and the second clamp element 31. Frequently, a ratcheting clasp 50 is used to lock the first clamp element 30 and the second clamp element 31 together.

Laparoscopic and thoracoscopic (collectively referred here as "endoscopic") instruments use a similar action. FIG. 2 shows an example of an endoscopic forceps 60 of the prior art. A first finger engager 70 and an opposing second finger engager 71 are used to actuate the mechanism. First finger engager 70 is rigidly mounted to the instrument body 72. Second finger engager 71 drives opposing clamp elements 80 and 81. A pivot 90 attaches the two clamp elements 80 and 81, such that actuation of second finger engager 71 forces clamp elements 80 and 81 together, thereby clamping a tissue between two clamp surfaces 85 and 86. As in FIGS. 1A and 1B, endoscopic forceps 10 can be used to force a tissue apart. Clamp elements 80 and 81 are closed, inserted into a tissue, and then opened to tear the tissue.

For either instrument, forceps 10 or endoscopic forceps 60, a surgeon performs blunt dissection by closing the forceps, pushing the closed forceps into a tissue and then, optionally, opening the forceps inside the tissue, using the force applied by opening of the jaws of the forceps to tear the tissue apart. A surgeon thus proceeds to dissect a tissue by a combination of pushing into the tissue and opening the jaws of the forceps.

Blunt dissection is commonly used for wet and slick tissues, and the smooth, passive surfaces of most surgical instruments slide easily along the tissue, impairing the instrument's ability to gain purchase and separate the tissue. Furthermore, the surgeon has only limited control, being able only to jab, move sideways, or separate. An improved instrument for blunt dissection that could differentially separate soft tissues while not disrupting firm tissues would greatly facilitate many surgeries.

SUMMARY OF THE DETAILED DESCRIPTION

Embodiments disclosed herein include methods and devices for blunt dissection, which differentially disrupt soft tissues while not disrupting firm tissues. In particular, in one embodiment, a drive mechanism and components for a differential dissecting instrument for differentially dissecting complex tissue is disclosed. The drive mechanism for a differential dissecting instrument comprises an elongate rotary drive train having a first proximal end and a second distal end, wherein the first proximal end is connected to a mounting base for attaching to a handle or a surgical robot. The drive mechanism also comprises a differential dissecting member configured to be rotatably attached to the second distal end, the differential dissecting member comprising at least one tissue engaging surface. The drive mechanism further comprises a mechanism configured to mechanically rotate the differential dissecting member about a substantially transverse axis of member rotational oscillation, thereby causing the at least one tissue engaging surface to move in at least one direction against the complex tissue. The at least one tissue engaging surface is configured to selectively engage the complex tissue such that when the differential dissecting member is pressed into the complex tissue, the at least one tissue engaging surface moves across the complex tissue and the at least one tissue engaging surface disrupts at least one soft tissue in the complex tissue, but does not disrupt firm tissue in the complex tissue.

In another embodiment, a differential dissecting member for dissecting a complex tissue is disclosed. The differential dissecting member comprises a body having a first end and a second end, with a central axis from the first end to the second end. The first end is configured to be directed proximally away from the complex tissue and configured to be engaged with a rotary drive train that moves the differential dissecting member such that the second end sweeps along a direction of motion. The second distal end comprises a tissue-facing surface that is configured to be directed toward the complex tissue. The tissue-facing distal-most surface comprises at least one tissue engaging surface comprised of an alternating series of at least one valley and at least one projection arrayed along the direction of motion on the tissue-facing surface such that the intersection of the at least one valley and at least one projection define at least one valley edge possessing a component of its direction perpendicular to the direction of motion. In one embodiment, the at least one valley edge is not sharp.

In another embodiment, a differential dissecting member (DDM) for differentially dissecting complex tissue is disclosed. The DDM comprises a body and a looped oscillating drive cable affixed to the body via a tortuous path. The tortuous path comprises at least one topologically constrained loop. The looped oscillating drive cable is configured to drive the body to high speed oscillations.

BRIEF DESCRIPTION OF THE FIGURES

FIG. 1A shows forceps used to grasp tissue;

FIG. 1B shows exemplary forceps used in blunt dissection to divide tissue;

FIGS. 3A through 3H-4 show an exemplary compact drive mechanism for a differential dissecting instrument for mounting on a handle, laparoscopic instrument, or surgical robot arm;

FIG. 3A shows an oblique view of a differential dissecting attachment (cover ghosted for clarity), having an oscillating differential dissecting member disposed at the end of an oscillatory drive train, including an integral motion filter;

FIG. 3B shows an oblique view of an oscillating differential dissecting member with motion filter;

FIG. 3C depicts a top view of an oscillating differential dissecting member with motion filter;

FIG. 3D shows a side view of an oscillating differential dissecting member with motion filter;

FIG. 3E shows an end view of an oscillating differential dissecting member with integral motion filter;

FIG. 3F-0 shows the vertical and horizontal components of the rotary motion of a portion of the rotary drive train, sectioned at a drive wheel;

FIGS. 3F-1 through 3F-4 show a cross-section of sequential motion of the drive train engaging and driving the motion filter of the oscillating differential dissecting member;

FIG. 3F-5 depicts a cross-section of the drive train showing the drive train engaging the motion filter via a roller bearing;

FIGS. 3G-1 through 3G-4 show the side view of sequential motion of the oscillating differential dissecting member engaging the drive train via the integral motion filter;

FIG. 3H-1 shows an oblique view of an oscillating differential dissecting member with an integral motion filter;

FIG. 3H-2 depicts a top view of an oscillating differential dissecting member with an integral motion filter;

FIG. 3H-3 shows a side view of an oscillating differential dissecting member with an integral motion filter;

FIG. 3H-4 shows an end view of an oscillating differential dissecting member with an integral motion filter;

FIGS. 3J-1 and 3J-2 depict oblique, top and side views of an oscillating differential dissecting member with a motion filter comprised of a hinged, rigid flat plate;

FIG. 4A shows an oblique view of the distal portion a differential dissecting instrument (cover transparent for clarity), having an oscillating differential dissecting member connected by a motion filter to the end of an multiple-motor rotary drive train comprised of a plurality of motors, connected in mechanical series, all delivering torque;

FIG. 4F-1 shows an oblique view of a plurality of motors with their driveshafts connected by torsionally stiff, flexible universal joints, each motor further covered and connected by its own housing segment, also articulated, and showing deflections, in two planes, from a straight line while delivering torque;

FIG. 4F-2 depicts the vertical and horizontal axes and center of rotation of an articulated housing joint, and its spatial relation to the housing segment and motor;

FIG. 5A-1 depicts a cable-driven, controllable differential dissecting member oscillating in a steady, symmetrical, sinusoidal fashion about a center of oscillation that points exactly forward about the longitudinal axis of the differential dissecting instrument;

FIG. 5A-2 depicts schematically the rotational position and the rotational velocity of the differential dissecting member through time;

FIGS. 5B-1 and 5B-2 depict a cable-driven, controllable differential dissecting member oscillating in a steady, symmetrical, sinusoidal fashion about a center of oscillation that points at a non-zero angle from the longitudinal axis of the differential dissecting instrument;

FIGS. 5C-1 and 5C-2 depict a cable-driven, controllable differential dissecting member oscillating in a symmetrical, sinusoidal fashion, but with a varying angular velocity profile, about a center of oscillation that points exactly forward about the longitudinal axis of the differential dissecting instrument;

FIGS. 5D-1 and 5D-2 depict a cable-driven, controllable differential dissecting member oscillating in a steady, symmetrical, sinusoidal fashion, but with a varying angular velocity profile, about a center of oscillation that points at a non-zero angle from the longitudinal axis of the differential dissecting instrument;

FIGS. 5E-1 through 5E-3 shows three stages in time of the operation of a controllable differential dissecting attachment located at the distal end of an endoscope, oscillating about a center of oscillation, creating a direction of dissection, and dissection in that direction, and showing arbitrary control of the direction of dissection thus permitting tunneling in arbitrary directions within tissues;

FIG. 6A-1 shows a differential dissecting member captured by, and driven to oscillate by, a continuous, circuitous loop of fine wire rope or cable passing through fenestrations made in the differential dissecting member for that purpose;

FIG. 6A-2 further shows the complete, internal, low-stress path of the loop of fine wire rope through the differential dissecting member, forming a "cow-hitch" (or "lark's head") knot, thereby topologically capturing the differential dissecting member without directly crossing itself;

FIG. 6B-1 through 6B-5 depict front, back, end, bottom, and profile views of a exemplary cable-retained differential dissecting member;

FIG. 6C-1 through 6C-3 depict oblique, side, and end views of a cable-retained differential dissecting member with a curved profile;

DETAILED DESCRIPTION

Specifically, "Differential Dissecting Attachments (DDA)" are disclosed. The term "differential" is used because a Differential Dissecting Attachment can disrupt Soft Tissue while avoiding disruption of Firm Tissue. The effector end of a Differential Dissecting Attachment, called a Differential Dissecting Member (DDM), can be pressed against a tissue comprised of both Firm Tissue and Soft Tissue, and the Soft Tissue is disrupted far more readily than the Firm Tissue. Thus, when a Differential Dissecting Instrument (DDI) equipped with a DDA bearing a DDM is pressed into a Complex Tissue, the Differential Dissecting Instrument disrupts Soft Tissue, thereby exposing Firm Tissues. This differential action is automatic—a function of the device's design. Far less attention is required of an operator than traditional methods for blunt dissection, and risk of accidental damage to tissues is greatly reduced.

For the purposes of this application, "soft tissue" is defined as the various softer tissues separated, torn, removed, or otherwise typically disrupted during blunt dissection. "Target tissue" is defined as the tissue to be isolated and its integrity preserved during blunt dissection, such as a blood vessel, gall bladder, urethra, or nerve bundle. "Firm tissue" is defined as tissue that is mechanically stronger, usually including one or more layers of tightly packed collagen or other extracellular fibrous matrices. Examples of firm tissues include the walls of blood vessels, the sheaths of nerve fibers, fascia, tendons, ligaments, bladders, pericardium, and many others. A "complex tissue" is a tissue composed of both soft tissue and firm tissue and can contain a target tissue.

Embodiments disclosed herein include methods and devices for blunt dissection, which differentially separate soft tissues while not disrupting firm tissues. We disclose a drive mechanism and related components for a differential dissecting instrument for hand use of attachment to surgical machines for the safe blunt dissection of complex tissues. A differential dissecting drive mechanism can grossly comprise first, an elongate member (which may be a housing) with a first, proximal end and a second, distal end, the first proximal end being associated with a mounting base suited to attaching to a surgical machine (for example a handheld laparoscopic instrument, or a surgical robot), second, a rotary drive train to generate rotation, third, a drive wheel to transmit that rotation, fourth, a motion filter to transform that rotation to oscillation, and finally a differential dissecting member to convert that oscillation into the dissection of complex tissues. The motion filter may further refine the rotational motion of the drive wheel into planar oscillation in one step, thereby greatly simplifying the design and manufacture of the differential dissecting attachment.

Figure 1A:
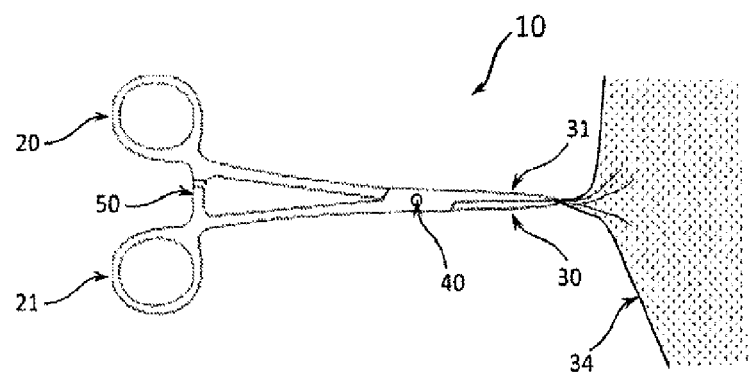
FIGS. 1A and 1B show examples of the prior art.
Figure 1B:
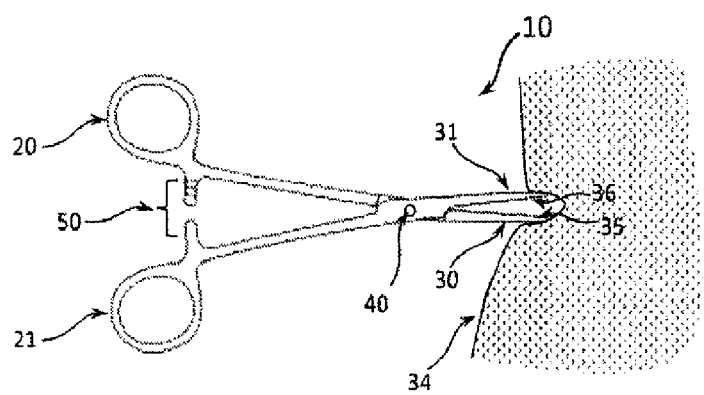
Figure 2:
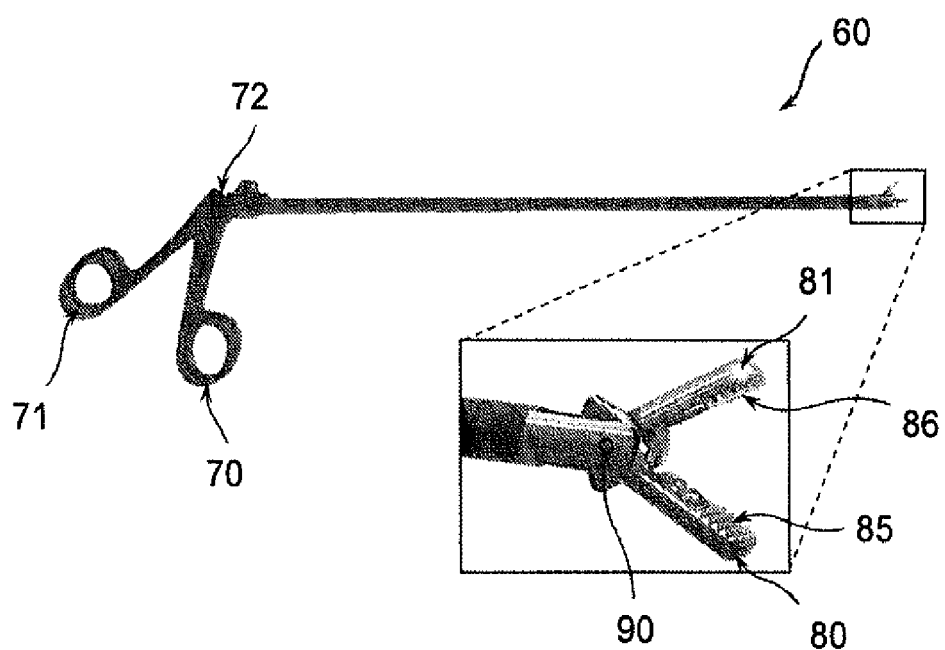
FIG. 2 shows laparoscopic forceps of the prior art.
Figure 3A:
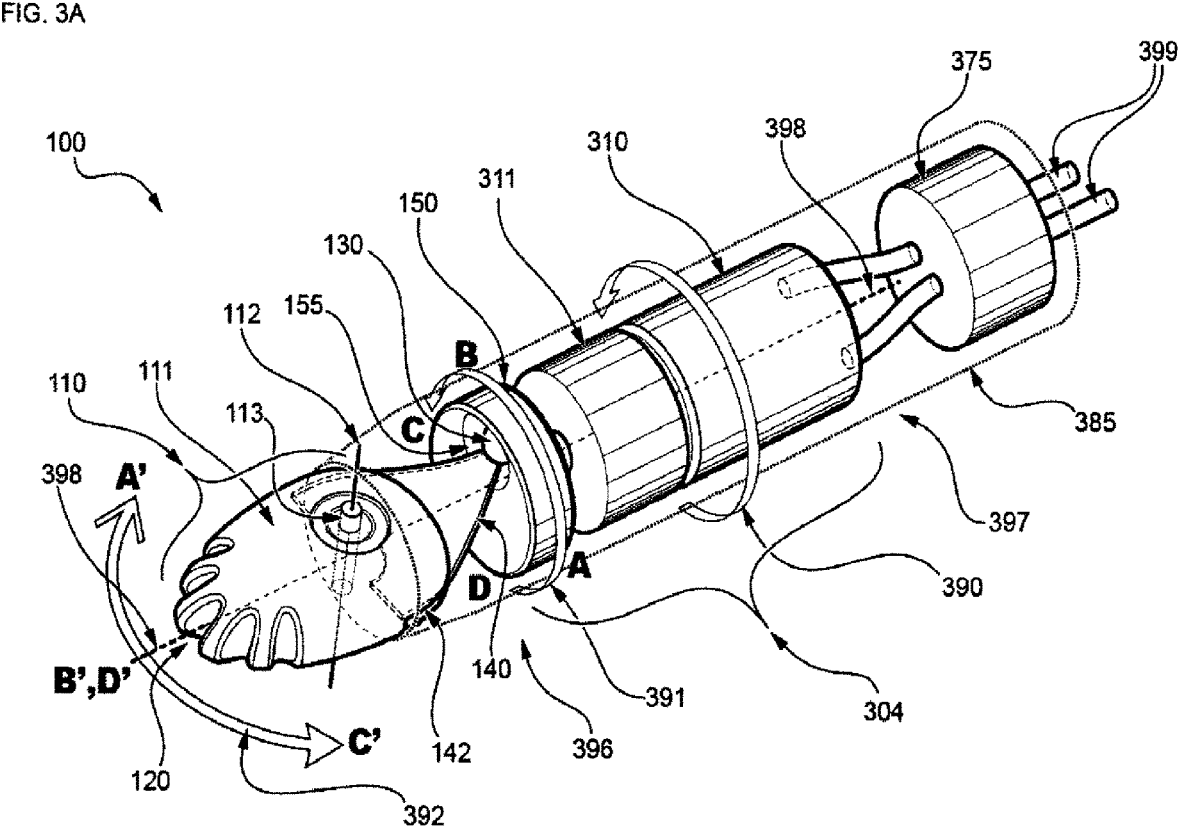

Referring to FIGS. 3A through 3J-2, we disclose one embodiment of an alternate drive mechanism 100 for driving oscillation of a DDM. This drive mechanism 100 can be attached to a handle or to a surgical robot, or to another surgical machine. FIG. 3A discloses drive mechanism 100 housed within a cover 385, the drive mechanism 100 further comprising a rotary drive train 304 supplying rotary motion 390 about a central, longitudinal axis 398, with a distal end 396 of the rotary drive train 304 substantially pointed at a complex tissue (not shown) and a proximal end 397 of the rotary drive train 304 substantially pointed at, and associated with, a mounting base 375; a drive wheel 150 with its axis coincident to the central, longitudinal axis 398 of the rotary drive train 304, and located distally to drive train 304, the drive wheel's rotation 391 supplied by the rotary drive train 304, the drive wheel 150 further comprising a drive-point 155 located at a non-zero radius away from the longitudinal axis 398 which is also the axis of drive wheel 150 rotation. A differential dissecting member 110 is positioned distally from the drive wheel 150 with the differential dissecting member 110 being rotatable about an axis of member rotational oscillation 112 that is substantially transverse to the central, longitudinal axis 398 of the rotary drive train 304. The differential dissecting member 110 further comprises a wedge-like body 111, an axle 113 that can be substantially coincident and concentric with axis of member rotational oscillation 112, at least one tissue-engaging surface 120 located distalmost on the device 100 and substantially pointed at a complex tissue (not shown), a torque-point 130 disposed proximally to the substantially transverse axis of member rotational oscillation 112 of the differential dissecting member 110, the torque-point 130 being operably associated with the drive-point 155, such that the torque-point 130 travels rotatably around the central, longitudinal axis 398 with drive wheel rotation 391; a substantially flat motion filter 140 operably connecting the body 111 of the differential dissecting member 110 and the torque-point 130, the motion filter 140 transmitting from the drive-wheel 150 through drive-point 155 only a planar component output motion 392 of the rotary motion input 391 of the torque-point 130 to actuate the differential dissecting member 110 in planar rotary oscillation about its substantially transverse axis of differential rotational oscillation 112. Thus, when the rotary drive train 304 continuously rotates the drive wheel 150, the drive-point 155 on the drive wheel 150 also rotates continuously, which continuously rotates the torque-point 130. The torque-point 130 is attached to the body 111 of differential dissecting member 110 by the motion filter 140, which in this embodiment is formed of an elastic planar member resisting in-plane deformation (and so transmits motion within that plane) but permits easy out-of-plane deformation (so not transmitting motion in that plane), which thus conveys only oscillatory planar motion 392 to the body 111 of differential dissecting member 110, which, thus oscillates about the substantially transverse axis of member rotational oscillation 112, causing the tissue engaging surface 120 to move in at least one direction 392 against the complex tissue, here in oscillatory planar motion 392, thereby this embodiment converts differential dissection member 110 oscillation into the dissection of complex tissues, disrupting at least one soft tissue in the complex tissue while avoiding disruption of firm tissue in the complex tissue.

It can be readily seen when referring to at least FIGS. 3A, 3F-0 through 3F-4, 3G-1 through 3G-4, 3J-1 and 3J-2, and 4A that one complete rotation of the rotary drive train 304 drives two passes (one in the opposite direction to the other) along planar motion of the tissue engaging surface 120 of the differential dissecting member 110 against the complex tissue. A motor 310 operating (i.e., rotating) at 100 Hz thus drives the tissue engaging surface 120 past the tissue to be dissected at 200 passes per second. Referring to the drive wheel rotation 391 of the drive wheel 150, if the rotation 391 begins at position A, the tissue engaging surface 120 of the differential dissecting member 110 is mechanically constrained to point to position A'. Thus, as the drive wheel 150 rotates to position B, the motion filter 140, here depicted as a planar leaf spring, easily deflects out of its own plane, and thus transmits to the differential dissecting member 110 only the planar component 392 (of drive wheel rotation 391) about the substantially transverse axis of member rotational oscillation 112, thus rotating the tissue engaging surface 120 to position B', in the same plane as position A'. As the drive wheel 150 continues its rotation 391 to position C, the tissue engaging surface 120 of the differential dissecting member 110 is rotated to position C', continuing the planar motion 392. As the drive wheel 150 advances to position D, the tissue engaging surface 120 moves to point D' (identical to position B'). Finally, as the drive wheel 150 returns to position A, the tissue engaging surface 120 of the differential dissecting member 110 also returns to position A', completing the cycle of oscillation of planar motion 392 of the differential dissecting member 110, and so the cycle of planar oscillation of the tissue engaging surface 120 against the complex tissue to be dissected.

Continuing to refer to at least FIG. 3A, the rotary drive train 304 may further be comprised of a direct current brushed electric motor, a brushless electric motor, a pneumatic motor, or the like; the rotary drive train 304 may further comprise a gearhead 311, for changing the torque and rotational velocity of the motor 310, for example to reduce the speed of the rotary motion 391 in exchange for higher torque at the drive wheel 150 and so increased authority at the tissue engaging surface 120, permitting more powerful dissections if desired. If the embodiment is electric, if the embodiment is electric, power may be supplied by wires 399 to the motor 310. The motion filter 140 can be formed of an elastic sheet, for example a leaf spring composed of, for example, metal or a rigid polymer.

In another embodiment of the multiple-motor rotary drive train 304 that addresses these needs, the rotary drive train 304 is composed of at least one commercial-off-the-shelf, integrated, small-diameter electric motor 310 and gearhead 311, achieving a compact device. One commercially available example of such a motor-gearhead combination is the 4-millimeter-diameter, 26-millimeter-long EC4 brushless motor from Maxon USA. A differential dissecting attachment constructed with a rotary drive train employing this or a similar motor is thus compact enough for attaching to the end of most instruments regularly employed for minimally invasive surgery.

The motion filter 140 can be formed of an elastic sheet, for example a leaf spring composed of, for example, metal or a rigid polymer. The material of the motion filter 140 may be distinct from that of the differential dissecting member 110, in which case it may be advantageous to provide a motion filter clamp 142 for holding the motion filter 140 therein. The substantially transverse axis of member rotational oscillation 112 might be comprised of a hole or cavity 114, for accepting an axle; if need be the hole 114 can be further fitted with a bushing or a roller bearing to reduce friction therebetween.

Figure 3B:
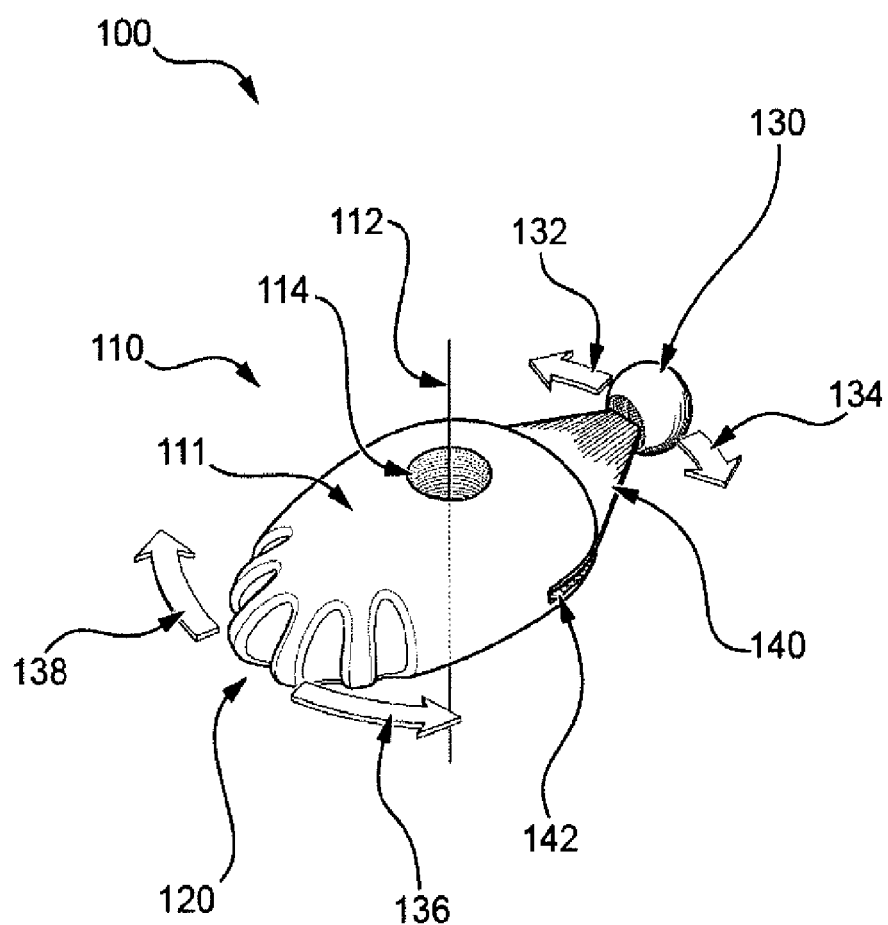

FIGS. 3B through 3F-5 show several views of an oscillating differential dissecting member 110 with motion filter 140. Referring first to FIGS. 3A and 3B, the oscillating differential dissecting member 110 has a body 111 that is rotatably associated with a substantially transverse axis 112; the body 111 may possess a bearing cavity 114 to further accept an axle 113 a bushing or roller bearing 115 (FIGS. 3A and 4A). The bearing cavity 114 may also be formed directly from the material of the wedge-like body 111 of the oscillating differential dissecting member 110, provided that a low-friction joint can be obtained between the body material and the material forming the axis 112; in FIG. 3A the axis 112 is coincident with and defined by an axle 113. In the embodiment depicted here, the tissue-engaging surface 120 is distal-most, as it dives into and safely dissects tissue. Opposite the tissue engaging surface 120 is the proximal-most portion of the oscillating differential dissecting member 110, namely the torque-point 130, which is operably associated with, and accepts rotational motion from, the drive wheel's 150 drive-point 155 (see FIG. 3A). The torque-point 130 can take many forms to mate with and accept the rotary input delivered via the drive-point 155. In one embodiment (shown), the torque-point 130 takes the form of a truncated ball, while the drive-point 155 (see FIG. 3A) can be a socket.

To attach the motion filter 140 to the body 111 of the oscillating differential dissecting member 110, the depicted embodiment features a motion filter clamp 142. The motion filter clamp 142 firmly grasps the distal-most end of the motion filter 140. The motion filter 140 can be any planar item that is flexible through its own plane, but resists shearing within its own plane. In the depicted embodiment, the motion filter 140 is formed out of spring steel. Thus, the rotary input from drive-point 155 succeeds in driving the torque-point 130 in circular motion about the long axis 398 of the drive mechanism 100. Due to the compliant bending of the spring steel motion filter 140 and due to the fixed rotation of the differential dissecting member 110 about the axis of rotation 112 (and also now referring also to FIG. 3F-0), that vertical component 126 of the circular motion 391 of the drive wheel 150, since it travels perpendicular to the plane of the motion filter 140, does not convey: there is no resulting planar motion 392 of the differential dissecting member 110. That horizontal component 124 of the rotational motion 391 that travels parallel to the plane of the motion filter 140, however, does convey to the differential dissecting member 110, as the spring steel is quite stiff within its plane and because the differential dissecting member 110 is free to rotate about its axis of rotation 112.

Thus, given a steady rotary motion 391 of the drive wheel 150 and the filtering of the motion components 124 and 126 by the motion filter 140, the differential dissecting member 110 oscillates in a sinusoidal fashion, as shown by arrows 136 and 138 in FIG. 3B. In more detail, the oscillating differential dissecting member 110 with its associated motion filter 140 is stiff as a whole within the plane defined by the substantially flat motion filter 140. When the torque-point 130 is driven in the direction indicated by arrow 132, the tissue-engaging surface 120 of the differential dissecting member 110 travels in the direction of arrow 136, and, when the torque-point 130 is driven in the direction indicated by arrow 134, the tissue-engaging surface 120 of the differential dissecting member 110 travels in the direction of arrow 138. Thus, a steady, constant rotational input 391 from the rotary drive train 304 (see FIG. 3A) produces bi-directional sinusoidal motion 392 at the tissue engaging surface 120.

Figure 3C:
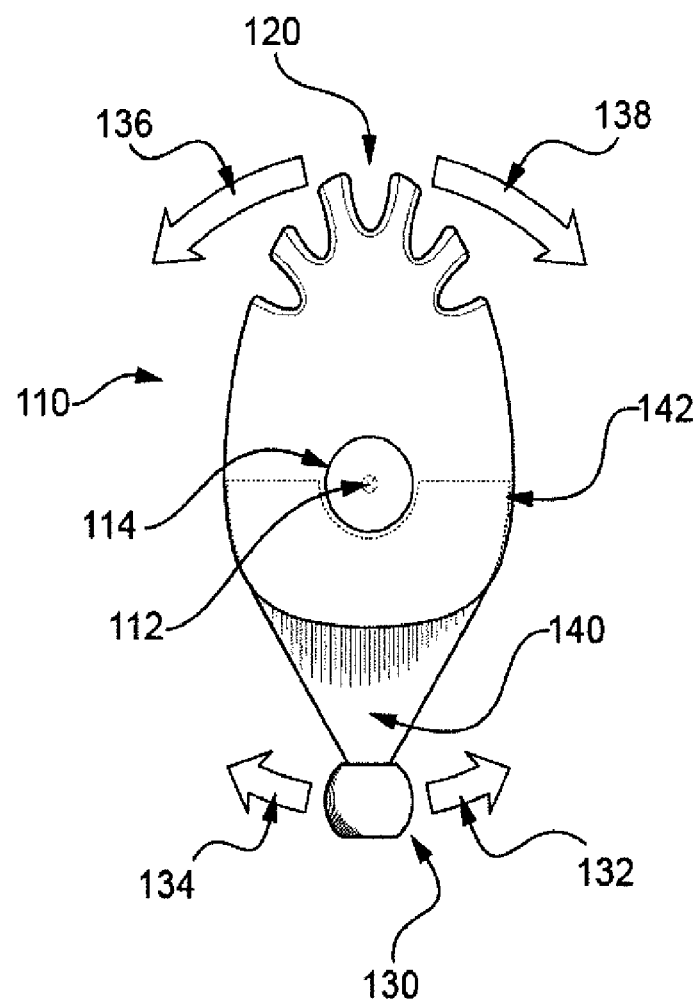

FIG. 3C depicts a top view (shown by itself for clarity) of an oscillating differential dissecting member 110 with motion filter 140. The horizontal components 132 and 134 (shown as 124 in the section view of FIG. 3F-0) of the rotary motion 391 of the torque-point 130, which are parallel to the plane of the page in this view, get transmitted via the motion filter clamp 142 to the body 111 of the oscillating differential dissecting member 110, driving the tissue engaging surface 120 as shown by arrows 136 and 138. However, the vertical component (element 126 in the section view of FIG. 3F-0) of the torque-point's 130 rotary motion that in this view passes through the plane of the page do not convey. Also note that it may be advantageous to manufacture the substantially flat motion filter 140 as a triangular beam. The motion filter 140 is essentially an end-loaded, cantilevered beam; the triangular form ensures that the stresses are constant along the length of the beam, preventing damage due to stress concentrations while the drive mechanism 100 operates at hundreds of cycles per second, under varying loads during surgery. Also, the triangular form of the motion filter 140 concentrates its mass nearest the substantially transverse axis of member rotational oscillation 112, reducing the energy required to oscillate the differential dissecting member 110.

Figure 3D:
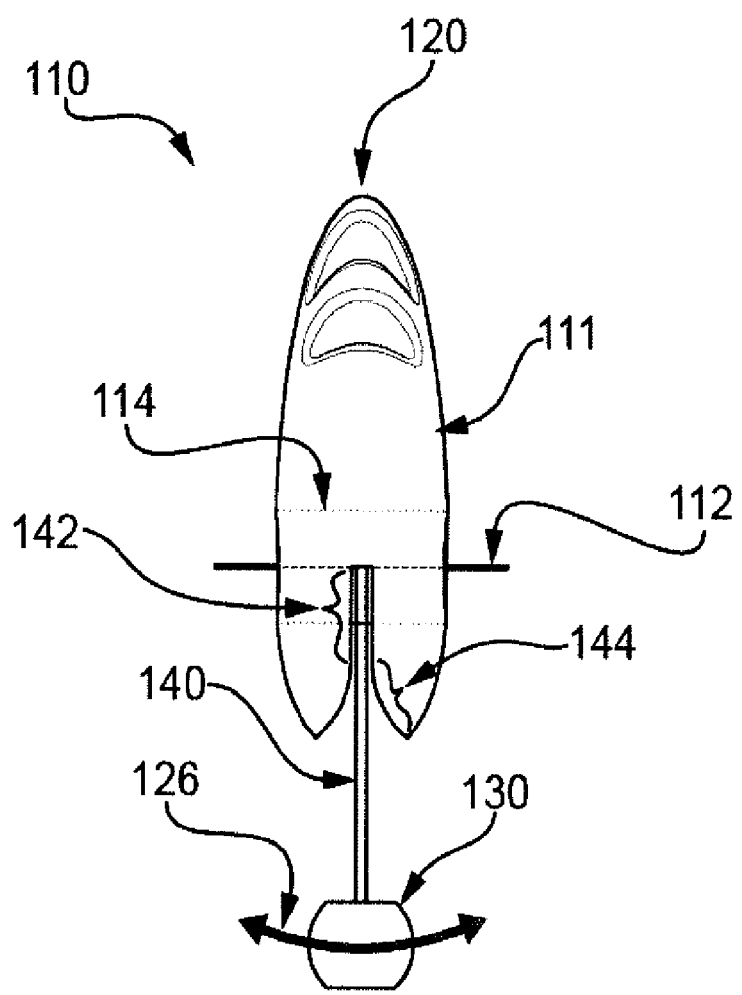

Referring now to FIG. 3D, this shows a side view of an embodiment of the oscillating differential dissecting member 110 with motion filter 140. The input motion (arrows 136 and 138 in FIGS. 3B and 3C) of the oscillating differential dissecting member 110 in the depicted view (FIG. 3D) is now into and out of the plane of the page. The compliant bending of the torque-point 130 of the motion filter 140 along vertical component 126 is left-and-right as depicted in FIG. 3D. The shape of the motion filter clamp 142 is more clearly depicted in this view. The body 111 of the oscillating differential dissecting member 110 further forms a profile cam 144 impinging on the travel of the motion filter 140.

Figure 3E:
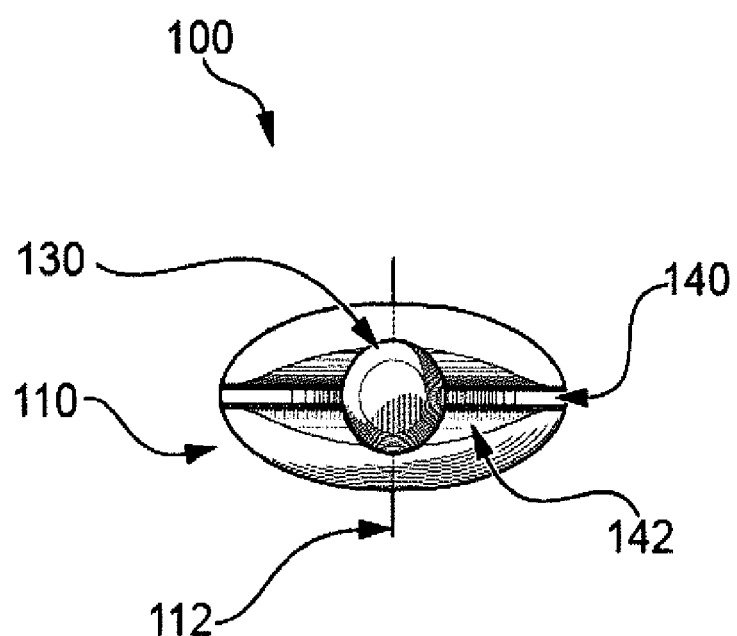

The shape of the profile cam 144 serves to control the loading of the motion filter 140; as the spring steel in this embodiment bends, it conforms to the shape of the motion filter profile cam 144. The shape of the profile cam 144 is arbitrary and can serve to preload the spring steel of the motion filter 140 to prevent backlash and keep the motion of the drive mechanism 100 smooth. FIG. 3E shows an end view of an oscillating differential dissecting member 110 with motion filter 140. The rotary travel of the torque-point 130 lies substantially in the plane of the page, as is more clearly shown in FIGS. 3F-1 through 3F-4.

Figures 0, 3F:
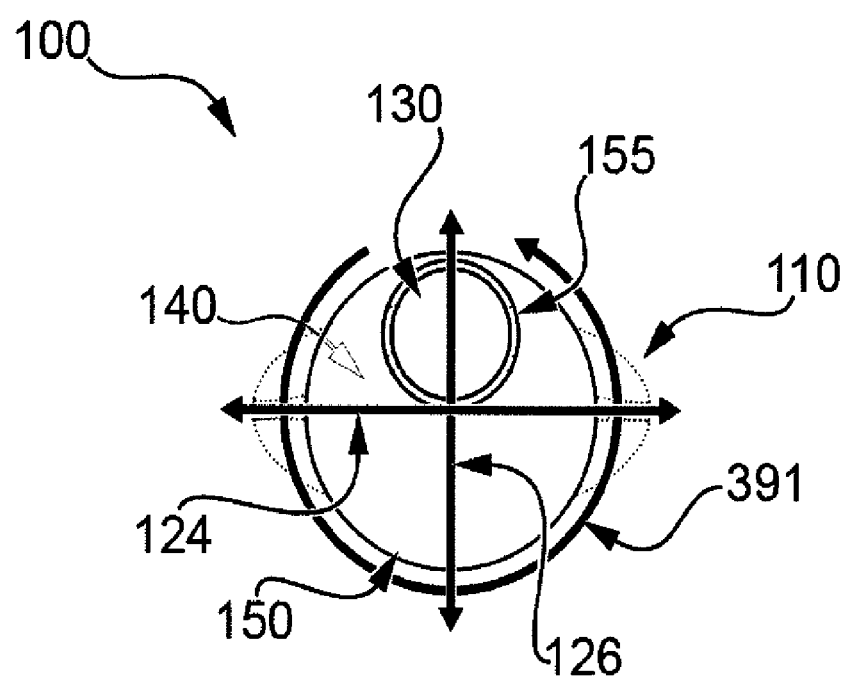

For clarity, FIG. 3F-0 depicts in section view looking distally the components of the rotary motion 391 (see also FIG. 3A) of the drive wheel 150 and drive-point 155 in relation to the differential dissecting member 110 and motion filter 140. The rotational motion 391 of the drive wheel 150 is comprised of two components: a vertical component 126, and a horizontal component 124. The motion filter 140, being an elastic flat plate, for example a steel leaf spring, bends easily out of its plane, easily accommodating the vertical component 126 of the rotary motion 391; since the substantially transverse axis of member rotational oscillation 112 (see FIG. 3A) resists the vertical component 126, no motion about axis 112 can occur. Since the motion filter 140, is an elastic flat plate possessing substantial rigidity within its own plane, and, since the substantially transverse axis of member rotational oscillation 112 expressly permits easy rotational motion in that same plane, all of (and only) the horizontal component 124 of the rotational motion 391 is transmitted from the rotary drive train 304 (see FIG. 3A) to the differential dissecting member 110, thus inducing oscillations in that plane, and so sweeping the tissue engaging surface 120 (see FIG. 3A) bi-directionally (parallel to the horizontal component 124) across the complex tissue to be dissected.

Figures 1, 3F:
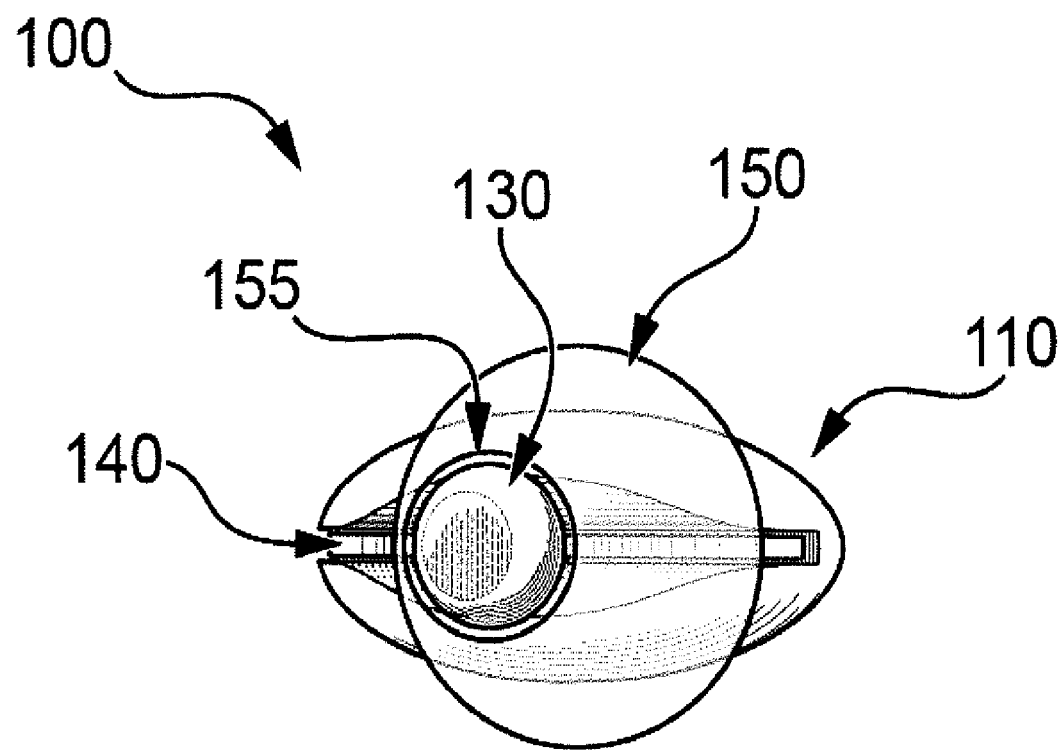
Figures 2, 3F:
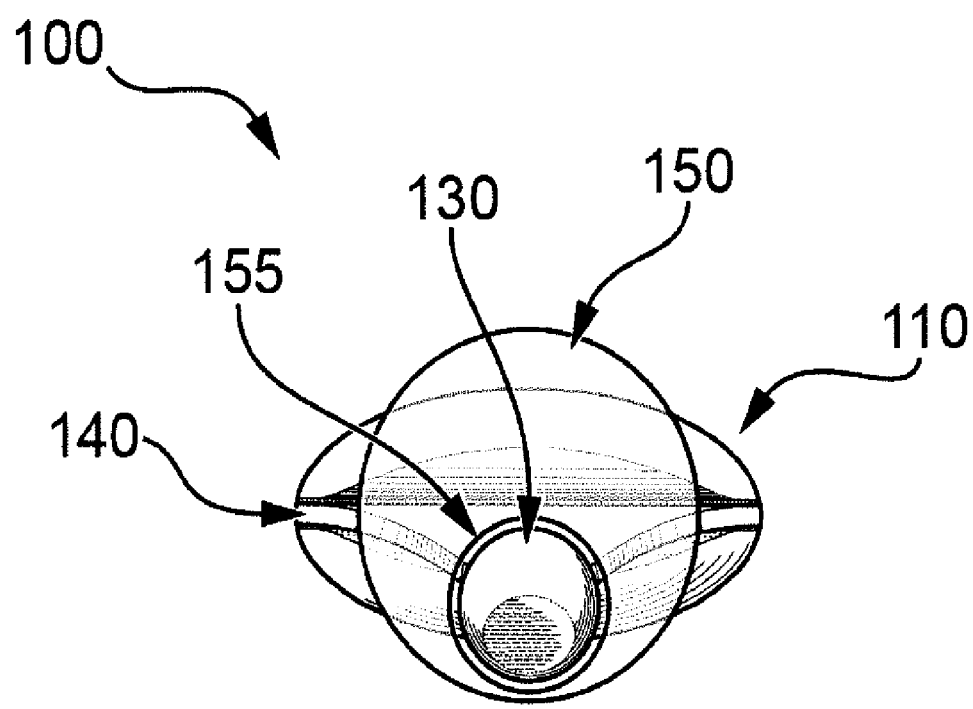

FIGS. 3F-1 through 3F-4 further depict in cross-section view through the drive wheel 150 the sequential (here, counterclockwise) motion of this portion of the rotary drive train 304 (see FIG. 3A). The drive wheel 150 drives the drive-point 155 which engages and so drives the torque-point 130, itself driving the motion filter 140 of the oscillating differential dissecting member 110. In FIG. 3F-1, the drive wheel 150 is rotated so that the drive-point 155 is to the viewer's left (at the 9 o'clock position). The torque-point 130, being engaged to the drive-point 155, has followed the drive-point 155, forcing the motion filter 140 to the left, which in turn forces the differential dissecting member 110 to rotate about the axis of member rotational oscillation 112 (see FIG. 3A). This necessarily forces the distal tissue engaging surface 120 (not visible in this view; it is at the opposite end of the differential dissecting member 110) to the right.

Figures 3, 3F:
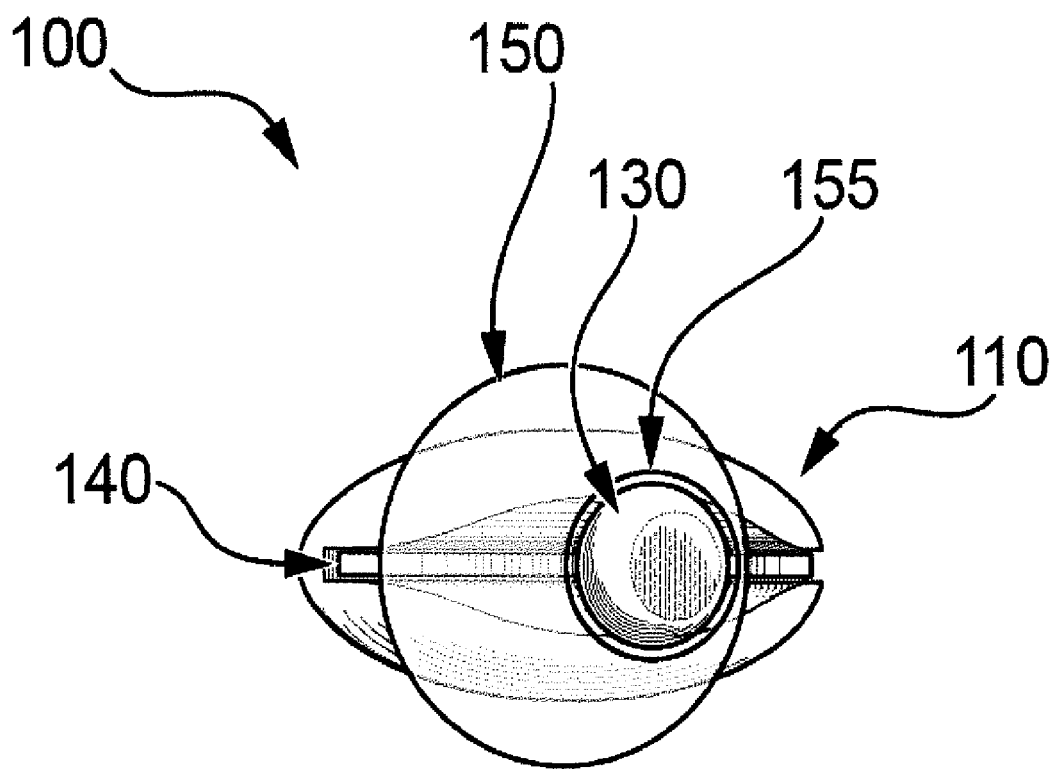
Figures 3, 3F, 4:
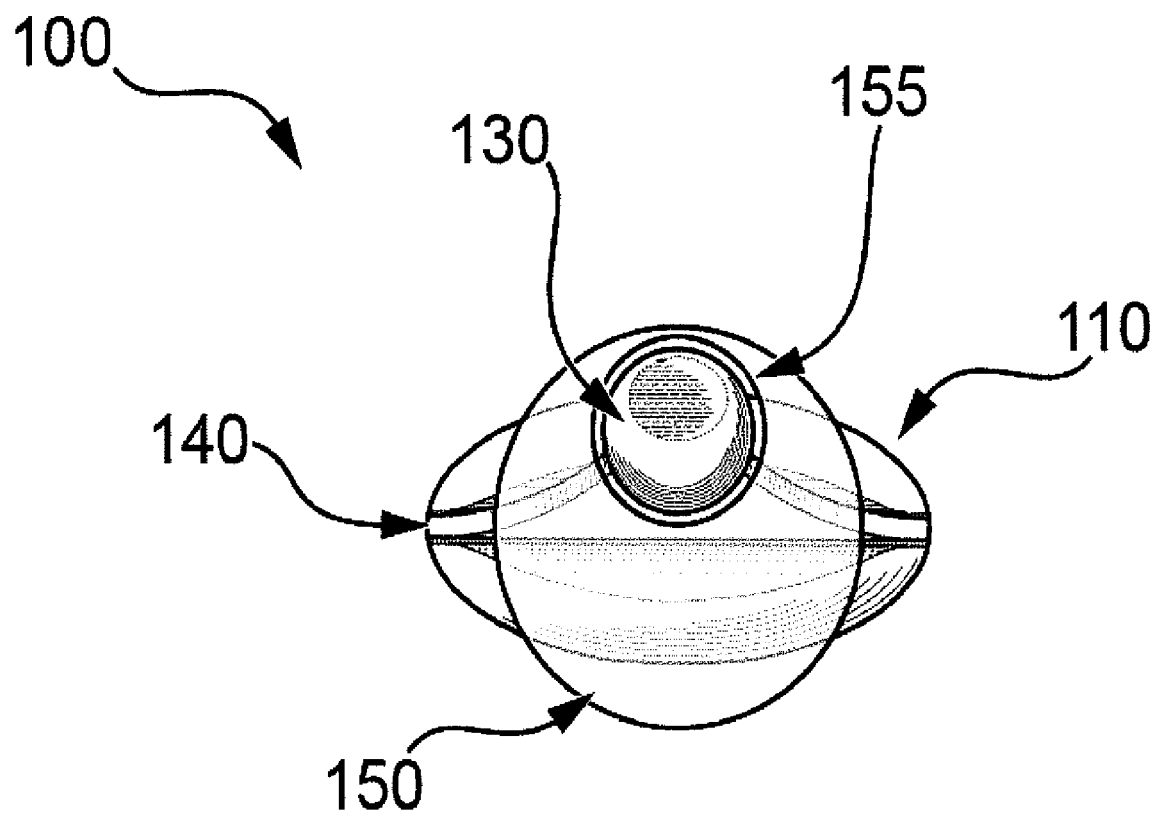
Figures 3, 3F, 4, 5:
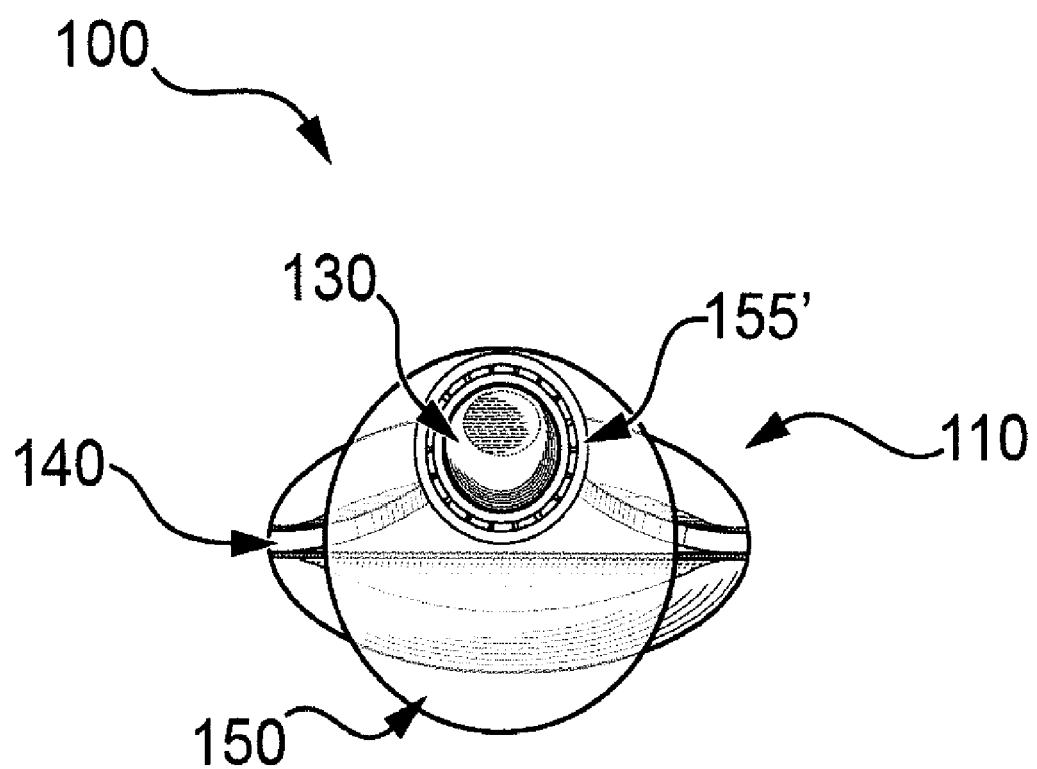

In FIG. 3F-2, the drive wheel 150 has rotated counterclockwise so that the torque-point 130 is at the bottom of travel (the 6 o'clock position); while the entire oscillating differential dissecting member 110 has returned to center. Note the downward-bent state of the motion filter 140, which has filtered out the (in this view) vertical component 126 (see FIGS. 3C and 3D) of the rotational motion 391 of the torque-point 130. In FIG. 3F-3, the drive wheel 150 (and so the drive-point 155, and the torque-point 130) has cycled counterclockwise around to the viewer's right (the 3 o'clock position), driving the tissue engaging surface 120 to the viewer's left. FIG. 3F-4 continues the cycle, with the drive-point 155, and the torque-point 130 rotating counterclockwise to the viewer's 'up' position (12 o'clock). Continuing rotational motion 391 clockwise will bring the drive wheel 150 and so the drive-point 155 and so the torque-point 130 to the nine-o'clock position, completing the cycle. The continuous rotation 391 of the drive wheel 150 that drives the non-rotating torque-point 130 means that frictional losses at the drive-point 155 could cut the efficiency of the drive mechanism 100. FIG. 3F-5 shows an embodiment of a drive mechanism 100 wherein a drive wheel 150 operably connects to a torque-point 130 via a drive-point 155' formed by a roller bearing, greatly reducing frictional losses due to relative rotation between the drive wheel 150 and the torque-point 130.

Figures 1, 3G:
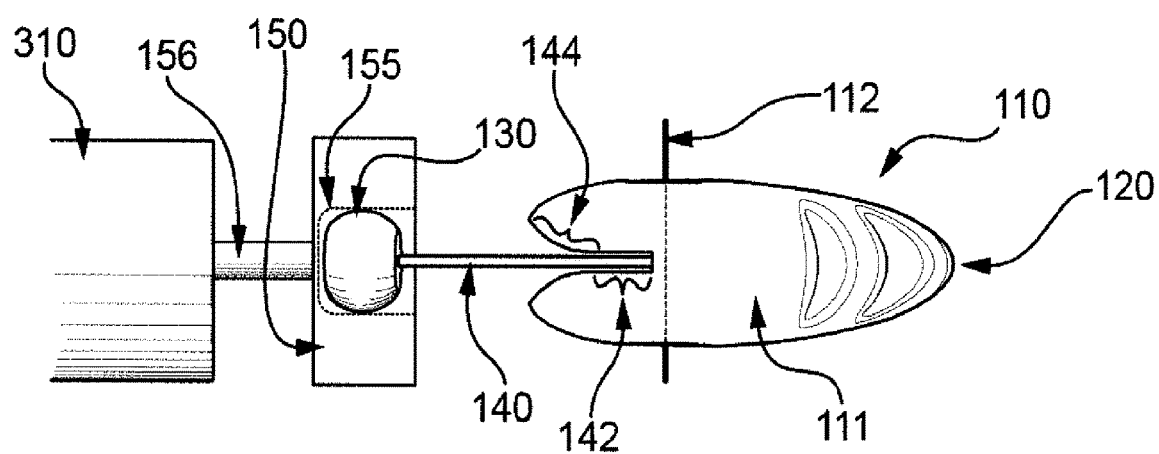
Figures 2, 3G:
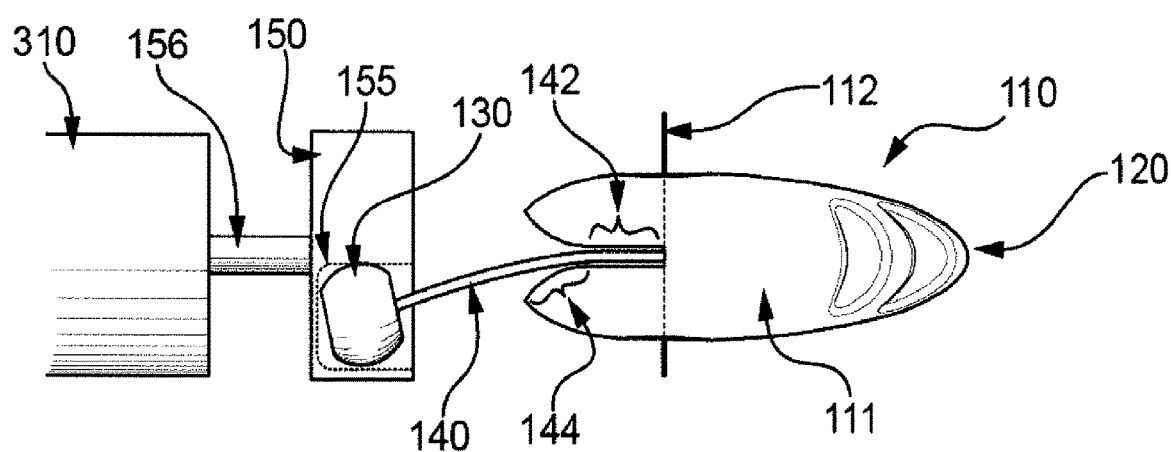
Figures 3, 3G:
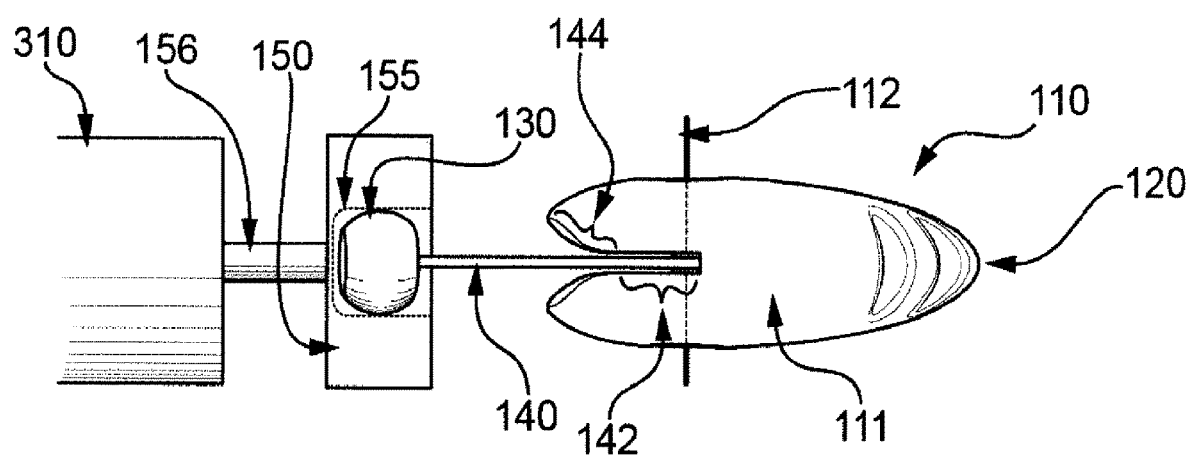
Figures 3, 3G, 4:
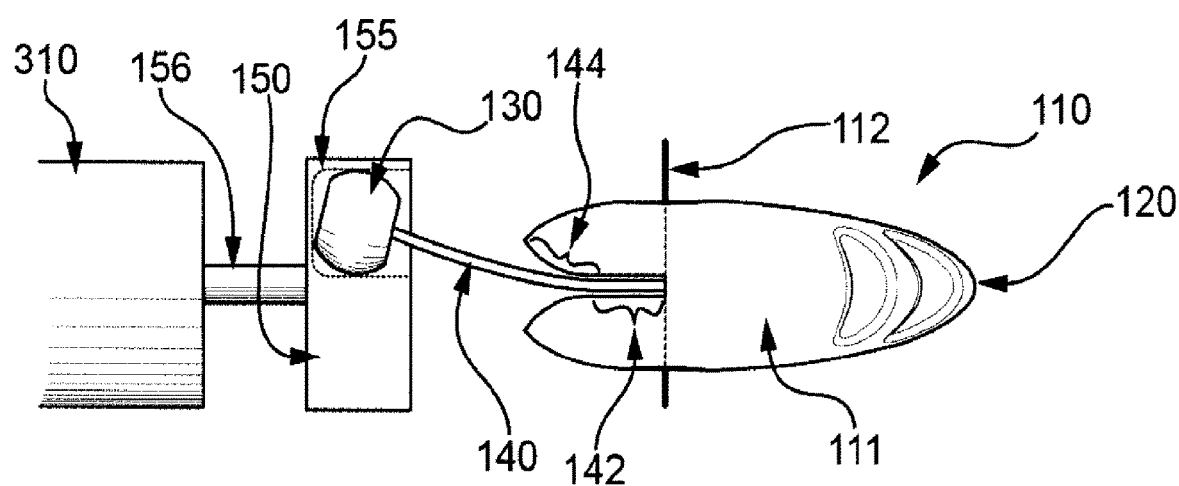

Referring now to FIGS. 3G-1 through 3G-4, we see the same process from a side view; the sequential motion of the oscillating differential dissecting member 110 oscillates due to its engaging the drive train 304 (shown partially here, and fully in FIG. 3A) via the motion filter 140. In the views of FIGS. 3G-1 through 3G-4, we can further see that the torque-point 130, here depicted as a truncated ball, tilts significantly within the drive-point 155, here depicted as a socket. Referring to FIG. 3G-1 (a side view of the device shown in FIG. 3F-1), a motor 310 has, via driveshaft 156, rotated the drive wheel 150 so that the drive-point 155 is farthest from viewer. The torque-point 130, being engaged to the drive-point 155, has necessarily followed the drive-point 155, forcing the motion filter 140 (in this embodiment, a leaf spring) to rotate away from the viewer, thus forcing the differential dissecting member 110 to rotate about the axis of member rotational oscillation 112 and so necessarily forcing the distal tissue engaging surface 120 toward the viewer. We can see that at this stage of the oscillatory cycle, the elastic, plate-like motion filter 140 is unbent; we can also see the motion filter clamp 140 formed in the body 111 (see FIG. 3A) of the differential dissecting member 110 and holding the motion filter 140. At this point, the profile cam 144 is not engaged.

In FIG. 3G-2, we see the side view of the stage depicted in FIG. 3F-2 where the motor 310 has caused (via driveshaft 156) the drive wheel 150 to rotate counterclockwise so that the torque-point 130 is now at the bottom of its rotational motion 391 (see FIG. 3A). The oscillating differential dissecting member 110 has returned to center, and at this moment the tissue engaging surface 120 points directly distally, in this view, to the viewer's right (equivalent to position B' and D in FIG. 3A). Note, however, the downward-bent state of the elastic, plate-like motion filter 140, which has filtered out the (in this view) vertical component 126 (see FIG. 3F-0) of the rotational motion 391 (see FIG. 3A) of the torque-point 130, so that the differential dissecting member 110 displays no rotation within the plane of the page. Note also the smooth round shape of the profile cam 144 is now engaged and is gradually supporting the distal portion of the motion filter 140, thus controlling the loading of the motion filter 140, here a steel leaf spring.

In the next view (FIG. 3G-3, a side view of the part of the oscillation cycle depicted in FIG. 3F-3), the motor 310 has rotated, counterclockwise, via shaft 156, the drive wheel 150 (and so the drive-point 155, and so the torque-point 130) toward the viewer. Again, as in FIG. 3G-1, the motion filter 140 is unbent. In this view the motion filter 140 has cycled counterclockwise around away from the viewer, driving the tissue engaging surface 120 away from the viewer. Again, we can see the motion filter clamp 142 formed in the body 111 of the differential dissecting member 110 and securely holding the motion filter 140, and, we can see that the profile cam 144 is not engaged.

Referring to FIG. 3G-4, complimenting FIG. 3F-4 above, we see now the complete cycle, with the drive-point 155, and the torque-point 130 rotating counterclockwise to the viewer's 'up' position. The motion filter 140 is clearly bent upward along vertical component 126 (which, due to the motion filter 140, contributes nothing to the oscillatory motion of the differential dissecting member 110). It can be seen that the bending of the motion filter 140 causes the torque-point 130 to rotate within the plane of the page in FIGS. 3G-1 through FIG. 3G-4. For this reason, we show that a preferred form of the torque-point 130 can be a sphere, ball, or portion thereof.

The embodiments shown can be run at high speeds; the continuous rotational motion 391 of the drive wheel 150 that drives the non-rotating torque-point 130 means, along with the tilting ball disclosed above, that frictional losses at the drive-point 155 could cut the efficiency of the drive mechanism 100. Thus, employing a spherical torque-point 130 captured in a roller bearing (for example as depicted in FIG. 3F-5) serving as the drive-point 155 may reduce these losses to a minimum. The examples given here are not limiting; any number of schemes will serve to mate the drive-point 155 with the torque-point 130, so long as the torque-point 130 is free to both rotate and tilt within the drive-point 155, or the motion filter 140 is free to tilt at its attachment to drive wheel 150 at drive point 155 (e.g. by a flexible joint, hinge, or pivot).

Figures 1, 3H:
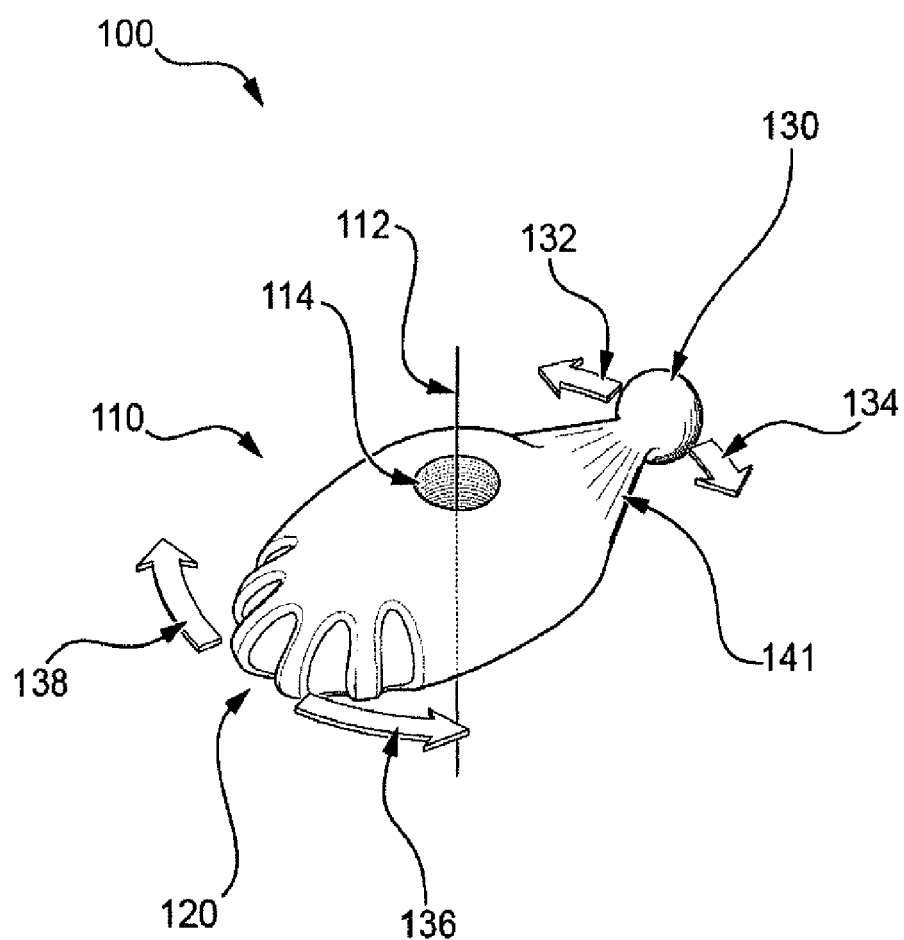
Figures 2, 3H:
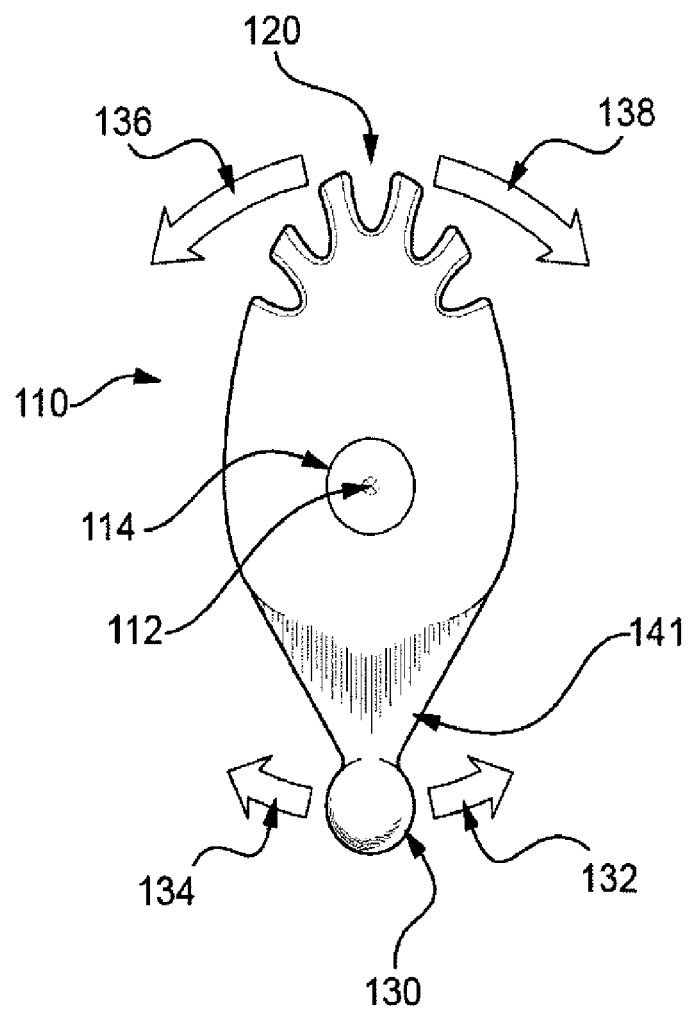
Figures 3, 3H:
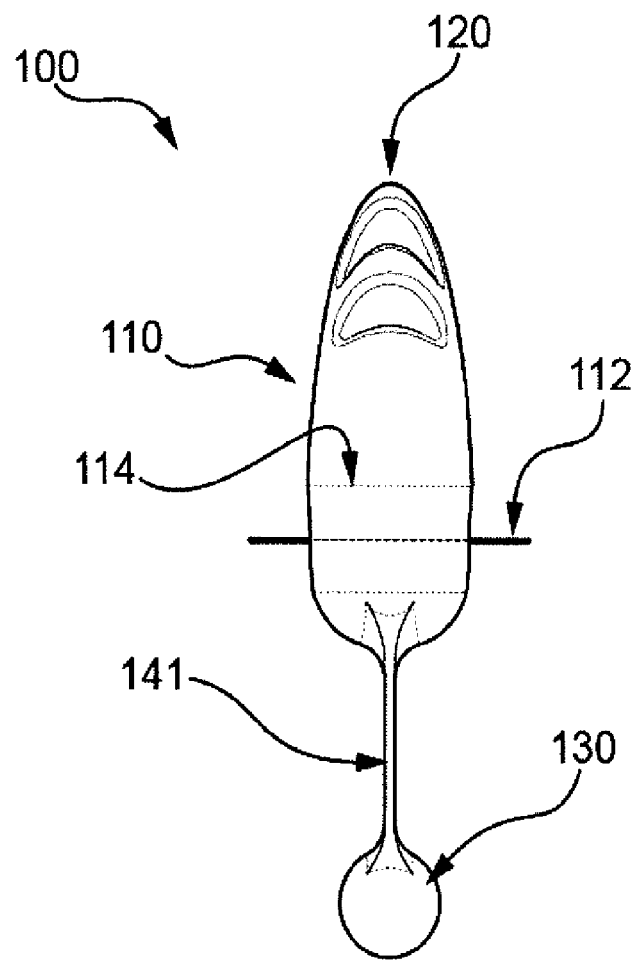
Figures 3, 3H, 4:
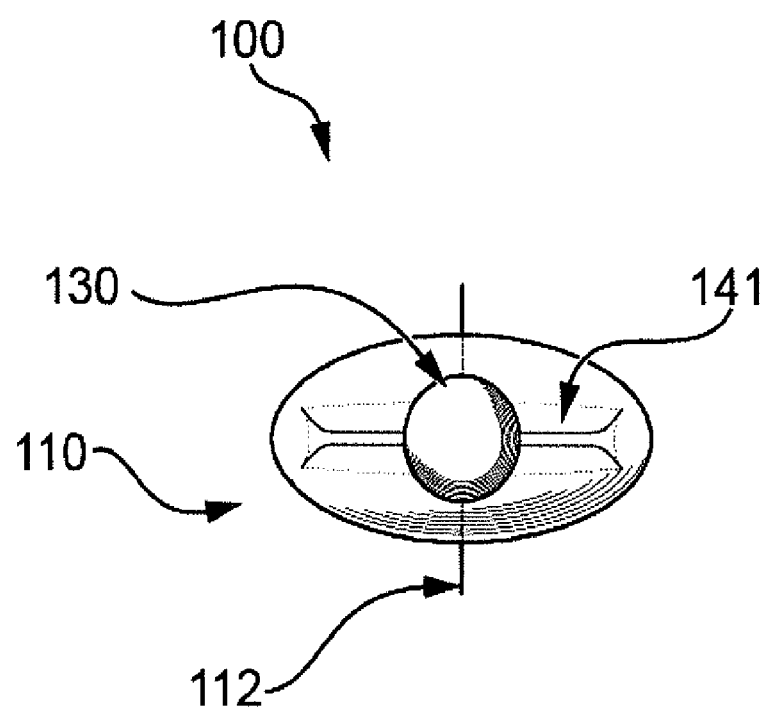

FIG. 3H-1 shows an oblique view of an alternative embodiment of oscillating differential dissecting member 110 with an integral motion filter 141. In this embodiment, the body 111 of the oscillating DDM 110 is molded to integrally include a flat elastic plane that serves as an integral motion filter 141, making the entire oscillating differential dissecting member 110 monolithic, which may possibly simplify manufacture.

FIGS. 3H-2, 3H-3, and 3H-4 depict a top view, a side view, and an end view, respectively, of the alternative embodiment of an oscillating differential dissecting member 110 with an integral motion filter 141. This embodiment can be molded out a single material (for example PEEK (polyetheretherketone)), as long as the elastic modulus is high enough to prevent buckling out-of-plane during transmission of the in-plane horizontal component 124 of the rotary motion 391 while filtering out the out-of-plane, vertical component 126 of the supplied rotary motion 391. The features of the integrally molded motion filter 141 are similar to that depicted in FIGS. 3B through 3E, save for the reduced complexity and time involved in producing the part for incorporation into a drive mechanism 100.

FIGS. 3J-1 and 3J-2 depict top and side views of another embodiment of an oscillating differential dissecting member 110 rotatable about substantially transverse axis of member rotational oscillation 112, further comprising a bearing cavity 114, and provided with an alternative motion filter 143 comprised of a rigid flat plate 143 attached to the differential dissecting member 110 via a hinge 149. This embodiment requires no elastic plates or gripping of same; a hinge is a well-understood mechanical feature. The operation of this motion filter 143 is much as was disclosed above, where the torque-point 130 engages the drive-point 155 of the drive wheel 150 driven in rotational motion 391 by the rotary drive train 304 (see FIGS. 3A, 3F-1 to 3F-4, and 3G-1 to 3G-4). This hinged motion filter 143 transmits the horizontal component 124 of rotational motion 391 without the vertical component 126. In this respect its operation is similar to those disclosed in FIGS. 3B to 3E, and 3H-1 to 3H-4), where motion of the torque-point 130 in the direction of arrow 132 drives the tissue engaging surface 120 in the direction of arrow 136, and motion of the torque-point 130 along arrow 134 results in the sweep of the tissue engaging surface 120 in the direction of arrow 138. Should elastic recoil be required, a hinge spring 148 is easily added to achieve some of the benefits disclosed above.

It will be understood by those skilled in the art that a number of substitutions can be made while preserving the spirit of a differential dissecting member driven via a motion filter, permitting planar oscillatory output of the tissue engaging surface. None of the embodiments disclosed above are meant to be limiting cases.

Referring to FIG. 4A, disclosed is a highly elongate compact drive train 400 enabling differential dissection in tight confines. Modern minimally invasive surgery has reduced the diameter (and burgeoning obesity has increased the length) of the surgical instruments required, demanding elongate, narrow, specialized tools for laparoscopic, endoscopic, thoracoscopic, and robotic procedures inserted through access ports, trocars and natural orifices. For example, it is commonplace for the inner diameters of trocars to be as small as 8, 5, and even 3 millimeters. It can be challenging to provide sufficient torque in instrument shafts of these diameters using one of even the best available motors. In addition, the newer instruments sport articulating shafts, the better to maneuver in tight spaces, but requiring mechanisms that use up much of what remains of the internal space. Fitting mechanisms through articulating shafts pose stiff challenges. Perhaps because of these obstacles, minimally invasive surgical blunt dissection still employs at the ends of these instruments the same primitive forceps, probes, and cotton swabs. Disclosed herein is a compact rotary drive train comprised of a plurality of small electric motors with driveshafts emerging from both ends, laid end-to-end coaxially in a column, sharing a common axis, and further comprising couplings associating the distal end of one motor driveshaft with the proximal end of another, adjacent motor driveshaft, forming a mechanical series. Provided with matching handedness of rotation by properly matching the sense of the motor power leads, the torque output of such a mechanical series motor arrangement is proportional to the number of motors in the column. In this way any required torque can be added to a very narrow surgical instrument. This mechanical series motor can further be provided within a narrow diameter, elongate rigid steel tube, as is the norm for other minimally invasive surgical instruments. Disclosed herein is how these can form articulated instrument shafts well-suited to the contortions of minimally invasive surgery.

FIG. 4A shows an oblique view of the components of a highly elongate compact drive train 400 comprising the distal portion of a differential dissecting instrument for attaching to a handle or to a surgical robot. The highly elongate compact drive train 400 is not dissimilar in part to the device depicted in FIG. 3A, save for the distinguishing features disclosed below. The highly elongate compact drive train 400 comprises a longitudinal axis 398 having a first, proximal end 397 that may be associated with a mounting base 375 facilitating attachment to a handheld surgical instrument or surgical robot, and a second, distal end 396 directed at a complex tissue to be dissected, and associated with an oscillating differential dissecting member 110. The two ends of the highly elongate compact drive train 400 are connected on the outside by a housing 385 (shown transparent for clarity), and largely occupied on the inside by a multiple-motor rotary drive train 305, and an oscillatory drive mechanism 303 nearer the distal end 396. The multiple-motor rotary drive train 305 is comprised of a plurality of double-shafted motors 310 (where each motor 310 is affixed to the housing 385, and each motor 310 further possesses a drive shaft 314 emerging from both ends of motor 310). The adjacent ends of each adjacent motor 310's drive shafts 314 are coaxially connected and rotationally locked to one another by torsionally stiff, flexible joints 313, so that the entire multiple-motor rotary drive train is connected in mechanical series. Further the drive shafts all rotate as one unit, with every motor 310 rotationally phase-locked to the others, such that all motors rotate at the same speed in the same direction 360.

In this embodiment, the differential dissecting member 110 possesses a body 111 and is located rotatably about a substantially transverse axis of member rotational oscillation 112 (which may be comprised of an axle 113) at the distal end 396 of the highly elongate compact drive train 400. The differential dissecting member 110 also connects operably to the oscillatory drive mechanism 303. The oscillatory drive mechanism 303 is itself comprised of (beginning proximally) a drive wheel 150 operatively associated with, and rotated by, the distal-most end 396 of the multiple-motor rotary drive train 305, the drive wheel further comprising a drive-point 155 located at a non-zero radius from the longitudinal axis 398 (which is also the axis of drive wheel 150 rotation). The drive-point 155 engages, captures and drives in rotation 391 about long axis 398 a torque-point 130, which in this embodiment forms the proximal-most extent of a motion filter 140. The motion filter 140 is fixed to the body 111 of the differential dissecting member 110 by a motion filter clamp 142. The differential dissecting member 110 possesses at least one tissue-engaging surface 120 (directed at a complex tissue to be dissected).

The entirety of the series of motors 310 are appropriately connected by power cables 399 according to the type of motor used, and providing the power for dissecting complex tissue. The embodiment depicted also includes a gear head 311 operatively associated with the distal end 396 of the multiple-motor rotary drive train 305 and rotated by it, and the proximal-most portion of the oscillatory drive mechanism 303. This allows the multiple-motor rotary drive train 305 to run at high rotational frequencies while the oscillatory drive mechanism 303 can cycle at lower rotational frequencies, with enhanced torque 390 (and so, enhanced authority of the device during forceful blunt dissection).

Continuing to refer to FIG. 4A, rotation of the multiple-motor rotary drive train 305 drives rotation of the oscillatory drive mechanism 303, which imparts rotational motion 391 to the drive wheel 150, which in turn rotates the drive-point 155. The drive-point 155 captures and so also rotates the torque-point 130 comprising the proximal-most portion of the motion filter 140.

As disclosed above with the alternate drive mechanism 100 shown in FIGS. 3A and 3F-0, the motion filter 140 transmits only the co-planar component, i.e., the horizontal component 124 of the rotary motion 391 of the torque-point 130 to the body 111 of the differential dissecting member 110. As was the case with other embodiments of the device above, if we begin with the drive wheel rotation 391 of the drive wheel 150 at position A, the tissue engaging surface 120 of the differential dissecting member 110 will point at position N. As the drive wheel 150 is driven in rotation to position B, the motion filter 140 bends out of its own plane and transmits to the differential dissecting member 110 only the horizontal component 124 of drive wheel rotation 391. Restricted to rotate only about the substantially transverse axis of member rotational oscillation 112, the differential dissecting member 110 thus forces the tissue engaging surface 120 to point at position B', on center and pointing directly distally, aligned with the longitudinal axis 398. As the drive wheel 150 rotates on through to position C, the tissue engaging surface 120 of the differential dissecting member 110 sweeps on to point at position C', continuing the planar motion 392. As the drive wheel 150 further advances to position D, the tissue engaging surface 120 now moves to point D' (identical to position 13', and aligned again with the longitudinal axis 398 of the highly elongate compact drive train 400). Finally, as the drive wheel 150 continues its rotation 391, it cycles around back to position A, so the tissue engaging surface 120 of the differential dissecting member 110 also returns to position A', completing the cycle of oscillation of planar motion 392 of the differential dissecting member 110.

In this way, the cycle of bi-directional, planar oscillation of the tissue engaging surface 120 against the complex tissue to be dissected proceeds, disrupting at least one soft tissue in the complex tissue while avoiding disruption of firm tissue in the complex tissue. In this manner, the highly elongate compact drive train 400 converts electrical power input into the safe and rapid dissection of complex tissues by otherwise unwieldy laparoscopic instruments or surgical robotic arms, to enable improved surgical outcomes.

Figure 4B:
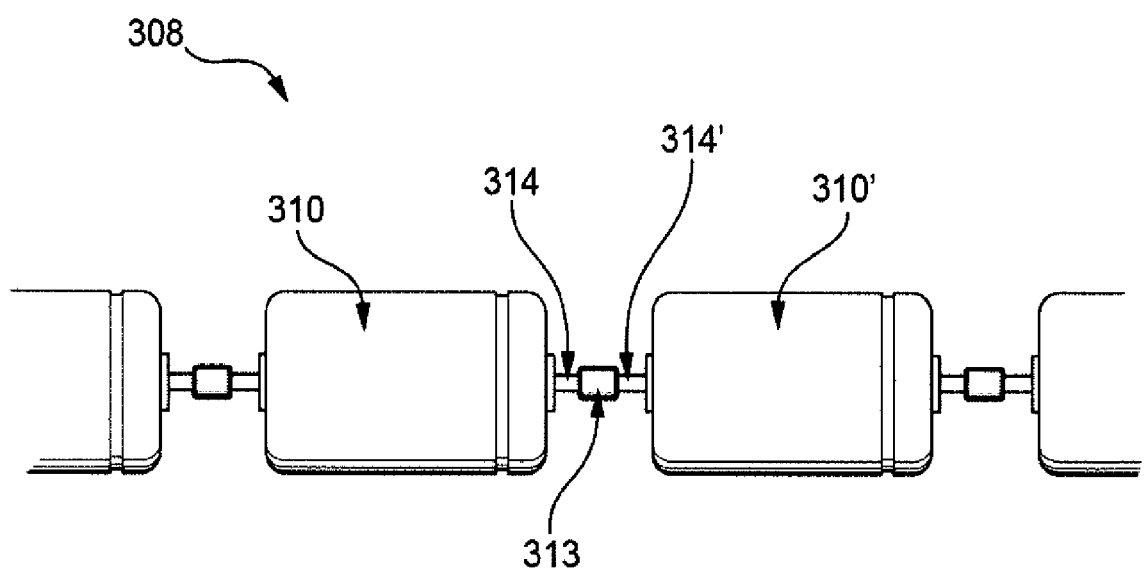
FIG. 4B shows a side view of a coaxial plurality of motors with their driveshafts connected by torsionally stiff, elastic joints, all arranged in a straight line and delivering torque.
Figure 4C:
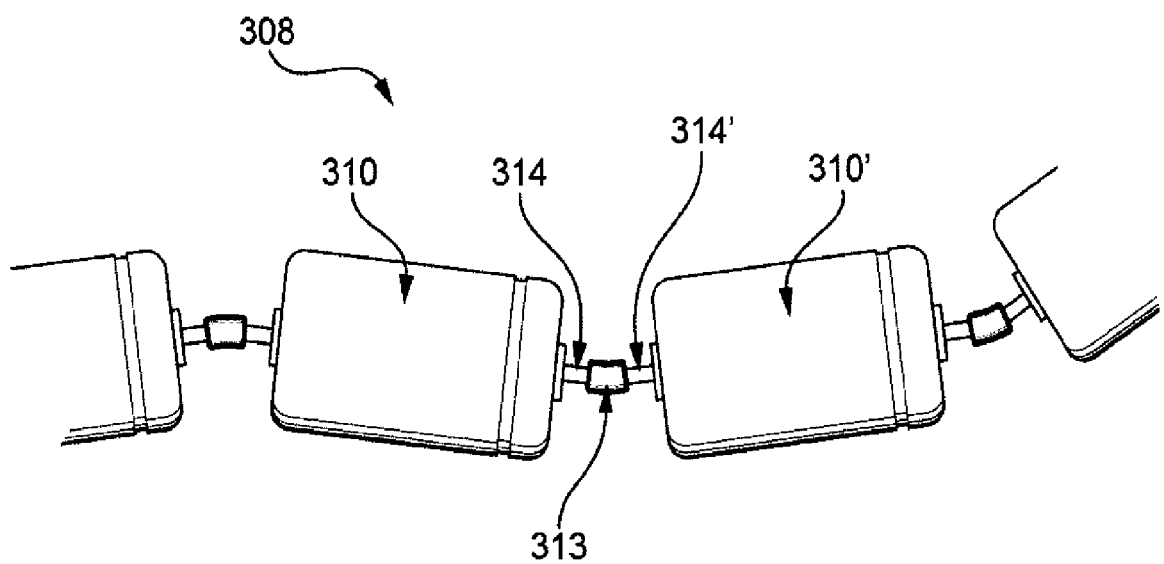
FIG. 4C shows a side view of a plurality of motors with their driveshafts connected by torsionally stiff, elastic joints, showing permitted deflections from a straight line while delivering torque.
Figure 4D:
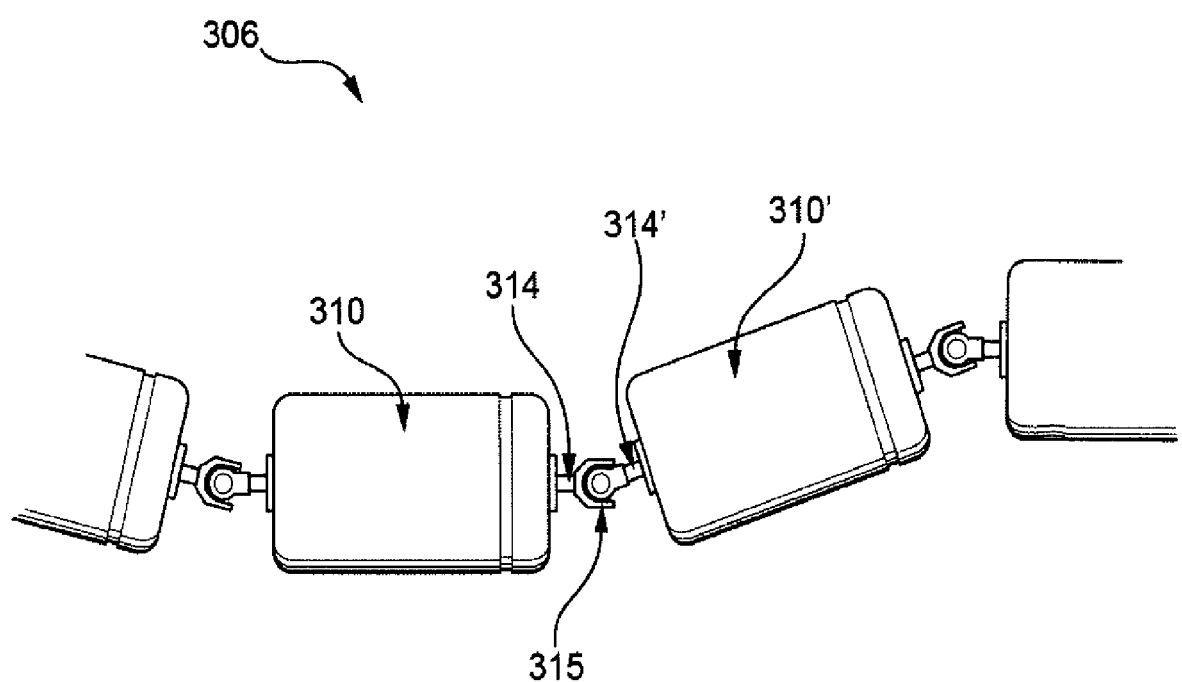
FIG. 4D shows a side view of a plurality of motors with their driveshafts connected by torsionally stiff universal joints, showing deflections from a straight line while delivering torque.
Figure 4E:
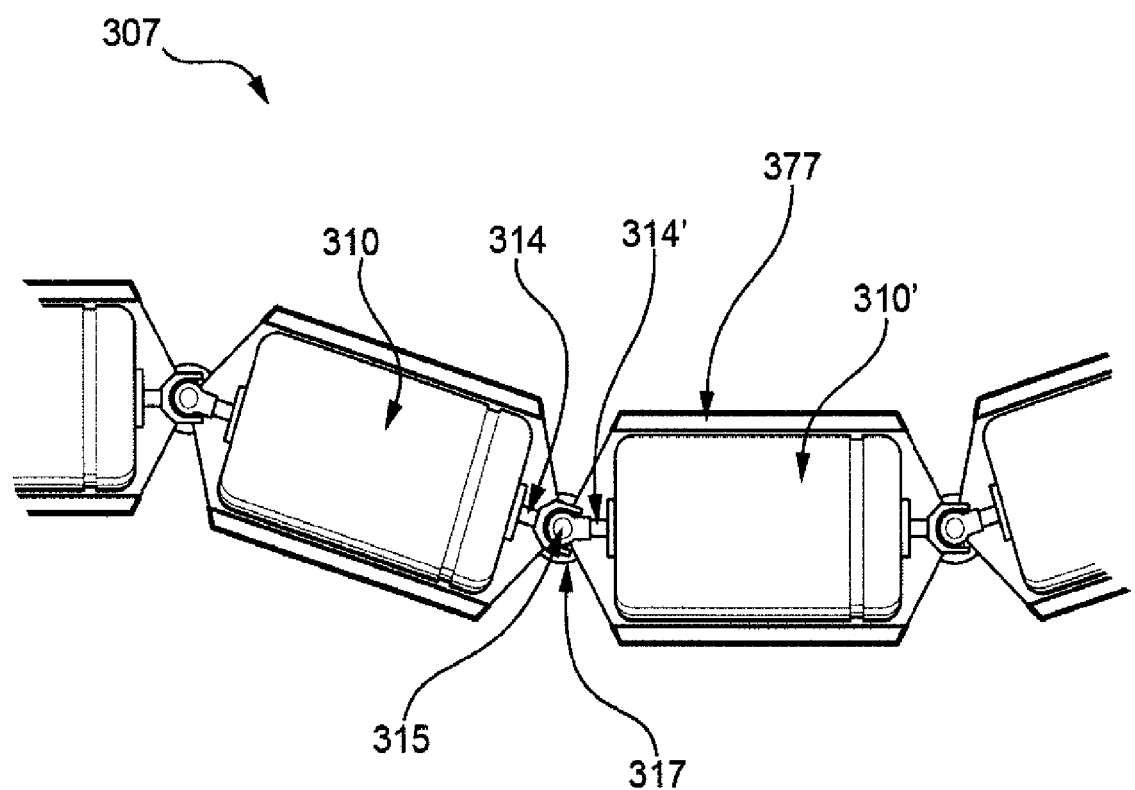
FIG. 4E shows a side view of a plurality of motors with their driveshafts connected by torsionally stiff universal joints, each motor further covered and connected by its own housing segment, also articulated, and showing deflections, in one plane, from a straight line while delivering torque.
Figures 1, 4F:
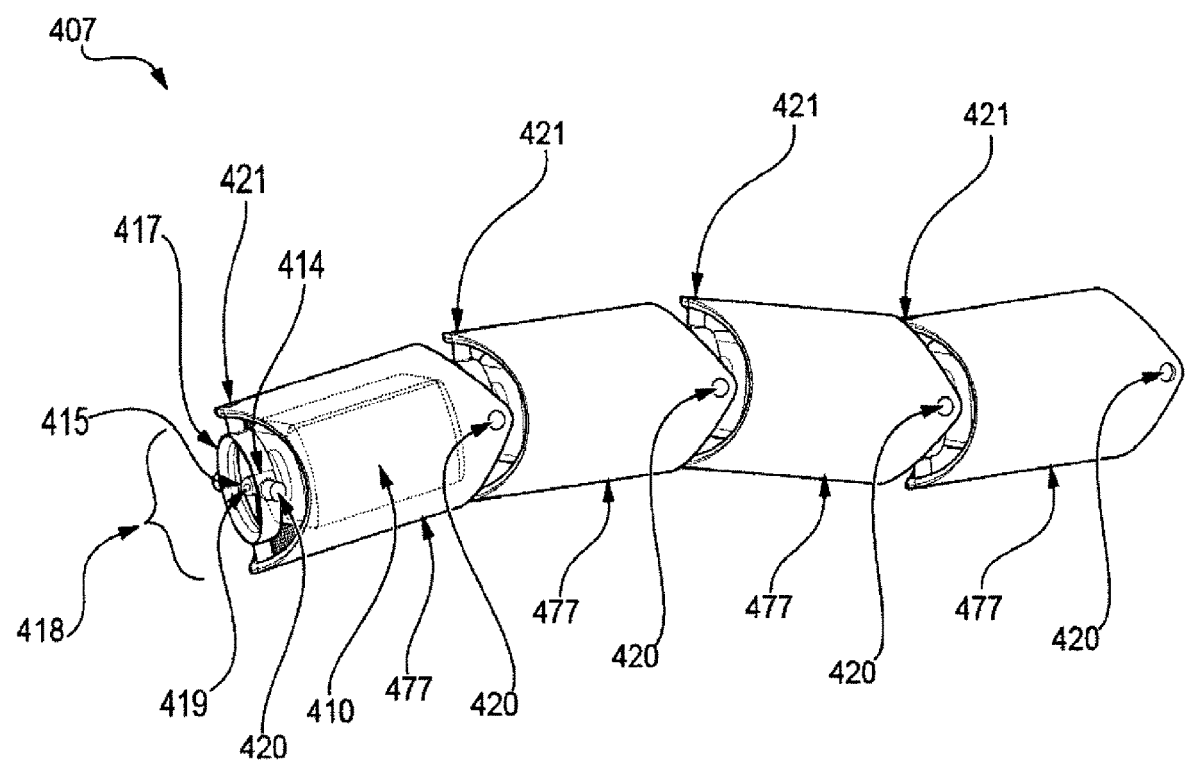
Figures 2, 4F:
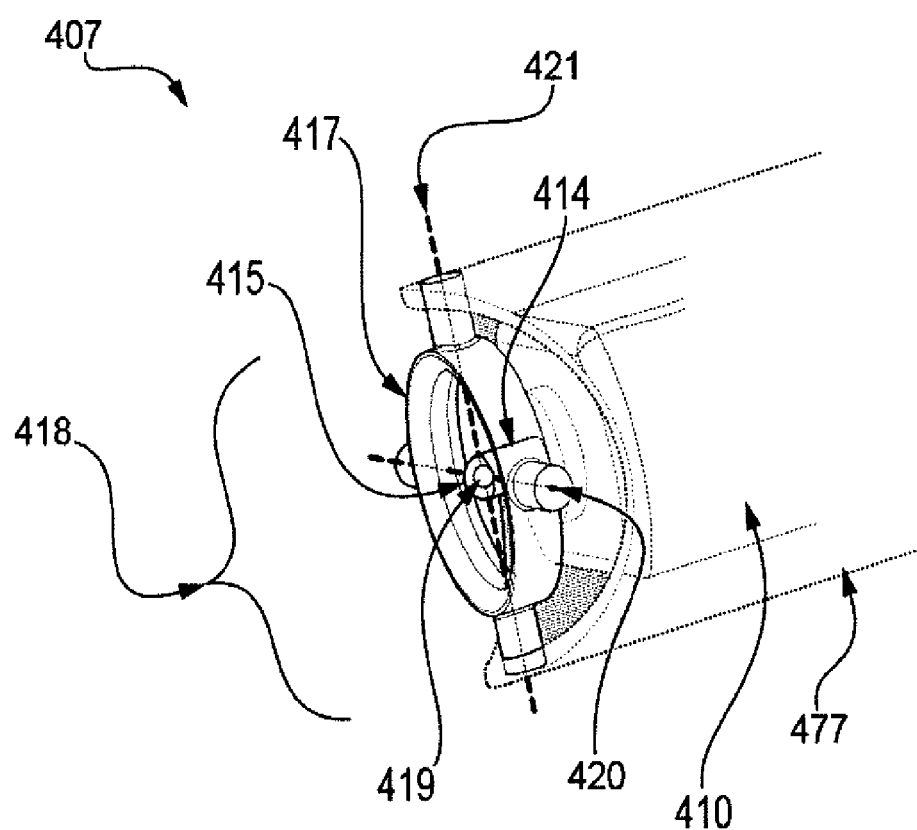
Figure 4G:
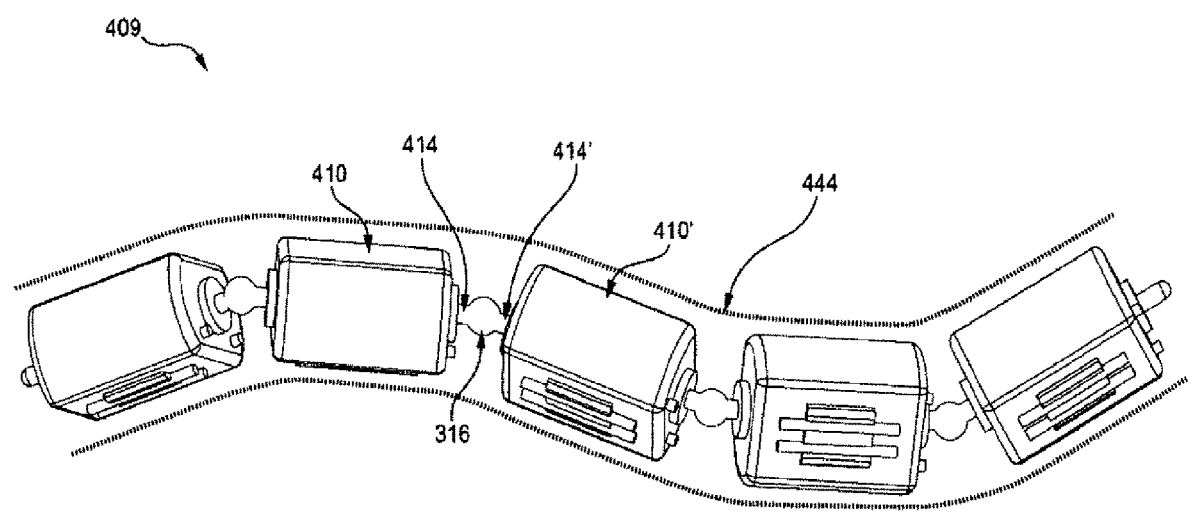
FIG. 4G shows an oblique view of a plurality of motors with their driveshafts connected by torsionally stiff, flexible universal joints, and showing deflections, in two planes at once, from a straight line, and showing rotational deflections of individual motors, all while delivering torque.

Looking at FIGS. 4B, through 4G, shown in FIG. 4B is a side view of an exposed multiple-motor rotary drive train 308 formed by a coaxial plurality of rotating motors 310, focusing in this view especially on the arrangement of two adjacent motors 310 and 310' with their adjacent driveshafts 314 and 314' connected by a reasonably torsionally stiff, flexible joint 313 (for example, made of an elastomeric tube, block, or rod, which tend to be quiet under way). At very low voltages, or at startup, very inexpensive motors (such as mass-produced DC brushed motors from manufacturers like Mabuchi Motors) can fail, due in part to stiction and cogging, difficulties well-known to those skilled in the art. With this arrangement, however, whatever motor 310 does, so does motor 310'. The inventors of this application have discovered that this arrangement (where motor 310 is connected to motor 310' by a flexible or compliant joint) appears to overcome cogging and stiction, possibly due to rotational misalignments between adjacent motors' rotors preventing cogging, or due to irregularities in adjacent motors startups combining to ensure a smoother, more reliable start. All of the depicted motors in this view are arbitrarily arranged in a straight line and all are actively delivering torque. Therefore, all of these motors are rotating at a single rotational velocity; this is a simple embodiment of the multiple-motor rotary drive train 305.

FIG. 4C shows a side view of the same actively rotating multiple-motor rotary drive train 308 disclosed above in FIG. 4B, but in this view, the plurality of motors 310 have been purposely deflected out of a straight alignment, though the motors are still coaxial at the joints 313 where the driveshafts 314 touch. With the driveshafts 314 and 314' of motors 310 and 310' still connected by the torsionally stiff, flexible joint 313, we can see how this arrangement permits reasonable deflections (and misalignments) of the multiple-motor rotary drive train 305 from a straight line while still actively delivering torque downstream, for example to an oscillatory drive mechanism 303. As long as the motors are prevented from relative rotations relative to one another, all of the motors in such an arrangement will remain rotationally phase-locked, turning together as one multiple-motor rotary drive train 305 (see FIG. 3A).

FIG. 4D shows a side view of a somewhat similar multiple-motor rotary drive train 306. In this embodiment, the plurality of motors 310 have their driveshafts 314 connected by universal joints 315, showing deflections from a straight line while delivering torque as one unit, similar to the situation depicted in FIG. 4C. Universal joints 315 are typically much more torsionally rigid than the elastomeric joints 313 shown in FIGS. 4B and 4C; the disclosed embodiments may usefully employ either. Other means to transmit torsion while bending are known in the art, including but not limited to sliding dog-bone joints, interlaced spider joints, bellows joints, and the like. The advantages of the use of universal joints 315 in multiple-motor rotary drive train 306 are that the energetic losses of deforming the material out of which are constructed the flexible joints in multiple-motor rotary drive train 308 above are that the universal joints 315 can be constructed with low-friction steel bearings. Further advantages of universal joints 315 is that the degree of permitted deflection may be larger than for flexible elastomeric joints 313, and that they usually withstand greater torque.

FIG. 4E shows a cross-sectional side view of an embodiment of a similar multiple-motor rotary drive train 307 to that disclosed in FIG. 4D, here comprising a plurality of motors 310 each with their driveshafts 314 connected to adjacent drive shafts by drive shaft universal joints 315. Each motor 310 in this embodiment, however, is further covered by its own associated housing segment 377 within which each motor 310 is fixed. Each housing segment 377 is also articulated at either end by a housing joint 317, surrounding the associated drive shaft universal joints 315 and thereby connecting each housing segment 377 to adjacent housing segments 377 and each drive shaft 314 to adjacent drive shafts 314. Thus, this embodiment of a multiple-motor rotary drive train 307 can deflect out of alignment as can the similar embodiments above, save that each motor 310 is fixed within its associated housing segment 377, providing structure to fight the reaction torque produced when the motor 310 energizes and rotates its drive shaft 314. So, as the multiple-motor rotary drive train 307 bends in one plane as depicted, the constituent motors 310 provide a combined maximum torque due to the stability provided by the housing segments 377. Further, the housing segments 377 provide a convenient surface to attach to a surgical robot or laparoscopic instrument, thus serving as an alternative mounting base 375 (see FIGS. 3A and 4A).

Illustrating this further, FIGS. 4F-1 and 4F-2 depict a multiple-motor rotary drive train 407 (and a component of same) with a plurality of motors 410 similar to those in FIG. 4E, each covered and supported by its own housing segment 477 and connected to each other by multiplanar concentric universal joints 418. The multiple-motor rotary drive train 407 is here shown deflecting in two planes at once, demonstrating three-dimensional flexibility appropriate for negotiating the twists and turns inside a patient. Also disclosed is a multiplanar concentric universal joint 419 combining a universal joint 415 that is connecting adjacent drive shafts 414 of adjacent motors 410, and, a similar two-axis housing segment joint 417. As is well-known to those skilled in the art, a universal joint is typically comprised of two axles oriented at right angles to one another, crossing at a geometric center, and both axles are typically oriented at right angles to the drive shafts with which they are associated, and, the axis of rotation of the associated drive shafts are aligned with that same geometric center. This is the case with the drive shaft universal joint 415.

Additionally, the housing segment joint 417 of this embodiment 407 is similarly comprised of two axes (defined by axles) 420 and 421, oriented at right angles to both one another and to the axis of rotation of the drive shafts 414, all crossing at a geometric center of rotation 419. What makes the multiplanar concentric universal joint 418 useful to the present device is that the universal joint 415 and housing segment joint 417 are arranged with common geometric centers of rotation. This means that the drive shafts 415 of the motors 410 are free to deflect while delivering torque despite being affixed in, and surrounded by, articulated rigid housing segments 477. To reiterate, each drive shaft universal joint 415 and associated housing segment joint 417 share a single geometric center of rotation 419 in all planes. Another consequence of this arrangement is that the length between these centers of rotation 419 is invariant owing to the rigid nature of the typically steel drive shafts 414. Thus, the length of the multiple-motor rotary drive train 407 cannot change despite the bending. This allows the surgeon performing the blunt dissection to apply both compressive loads down a confined passage, as is often required to develop forces against the tissue to be dissected, as well as to develop tensile loads, for example to withdraw the surgical instrument from the cavity so created.

Looking again at FIG. 4F-1, depicted in this figure are at least one housing segment joint 417, each comprising a ring supporting a vertically oriented pin joint 421 permitting rotation substantially in and out of the plane of the page, and a horizontally oriented pin joint 420, permitting rotation substantially within the plane of the page. The axes of the vertically oriented pin joint 421 and the horizontally oriented pin joint 420 cross exactly at a single geometric center of rotation 419 in all planes, the same geometric center of rotation 419 that is also used by the drive shaft universal joint 415. This is the arrangement that permits simultaneous phase-locked rotation of the drive shafts 414 of all of the motors 410 whilst the entire multiple-motor rotary drive train 407 deflects three dimensionally, permitting the surgeon to more easily access any desired internal space of the patient's body to perform safer blunt dissection of complex tissues.

FIG. 4F-2, shows in schematic form one housing segment joint 417 of a multiple-motor rotary drive train 407, a single center of rotation 419, and how it is formed by the convergence of the axes of the vertically oriented pin joint 421, the horizontally oriented pin joint 420, and the universal joint 415. One can again see that this arrangement permits the free deflection of the motors 410 whilst they are fixed within their housing segments 477, and simultaneously preserving phase-locked rotation of the entire multiple-motor rotary drive train 407.

To illustrate a final detail, FIG. 4G shows an oblique view of a multiple-motor rotary drive train 409 comprised of a plurality of coaxial motors 410 with their driveshafts 414 connected to one another and phase-locked by universal joints 416. Further, this embodiment 409 further comprises a flexible compliant sheath 444 (here shown in transparent form) covering the plurality of motors 410. The compliant sheath 444 is alternative to the rigid housing segments 477 from earlier embodiments. While the compliant sheath 444 permits all manner of deflections, including some rotational deflections of the motors 410, it still limits those rotational deflections, allowing the motors 410 to develop and deliver useful torque to supply downstream, for example to an oscillatory drive mechanism 303 (see FIGS. 3A and 4A). This view shows deflections from a straight line of motors 410 in two planes at once, and also rotational deflections of individual motors 410, all while phase-locked as before and delivering torque. Such an arrangement as this can be useful. A soft cover like the compliant sheath 444 may be preferable in some minimally invasive surgeries. One may also combine the compliant sheath 444 with the housing segments 477 for a smoother exterior while still preserving the full authority of the more rigid housing segments 477. The compliant sheath 444 and the housing segments 477 might also be fruitfully combined in irregular fashion, where neither motor cover scheme dominates the entire length of the multiple-motor rotary drive train 409.

As more surgeries are performed via minimally invasive surgical methods, working on ever-more-complex procedures with convoluted manipulations requires enhanced access capabilities, especially intricate, safe blunt dissections and tunneling around critical structures. Referring now to FIGS. 5A through 5E-3, disclosed are for surgical machines such as handheld laparoscopic instruments or surgical robots, embodiments of differential dissecting instruments and components for same that can perform blunt dissection of complex tissues in any desired direction. That is, the surgeon can steer the path of differential dissection at will, even remotely from the point of access (for example an incision, port, or a natural orifice), safely creating tunnels, pockets, and throughways of any desired shape in, around, or through complex tissues. Disclosed herein are steerable differential dissectors for differential dissection of complex tissues in any desired direction, operated remotely or directly.

Figures 1, 5A:
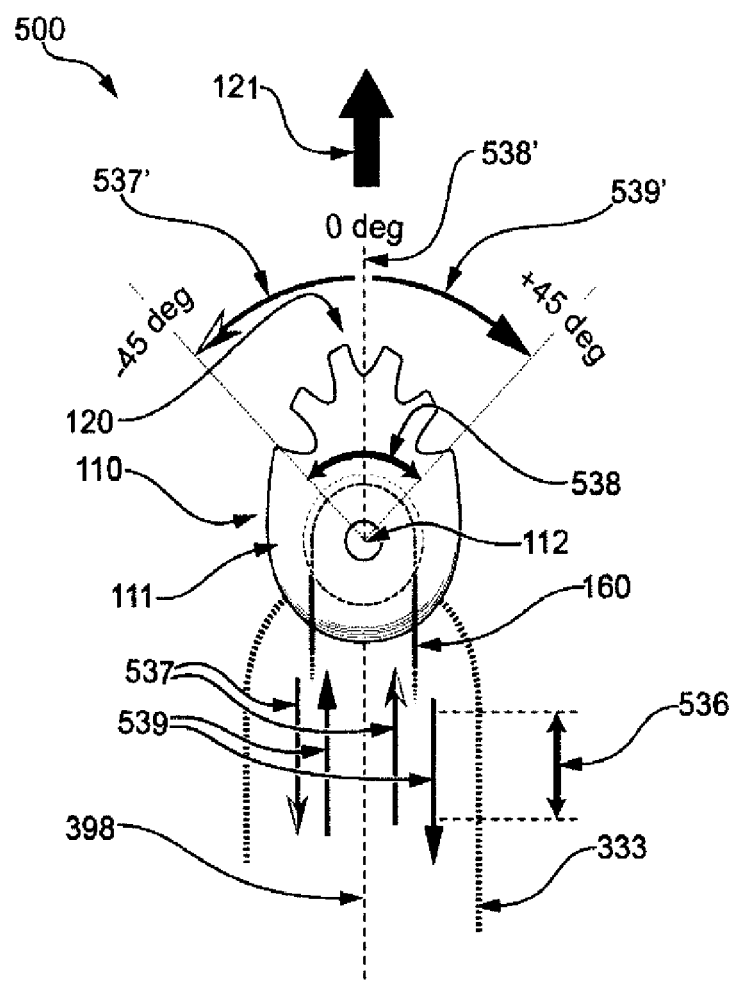
Figures 2, 5A:
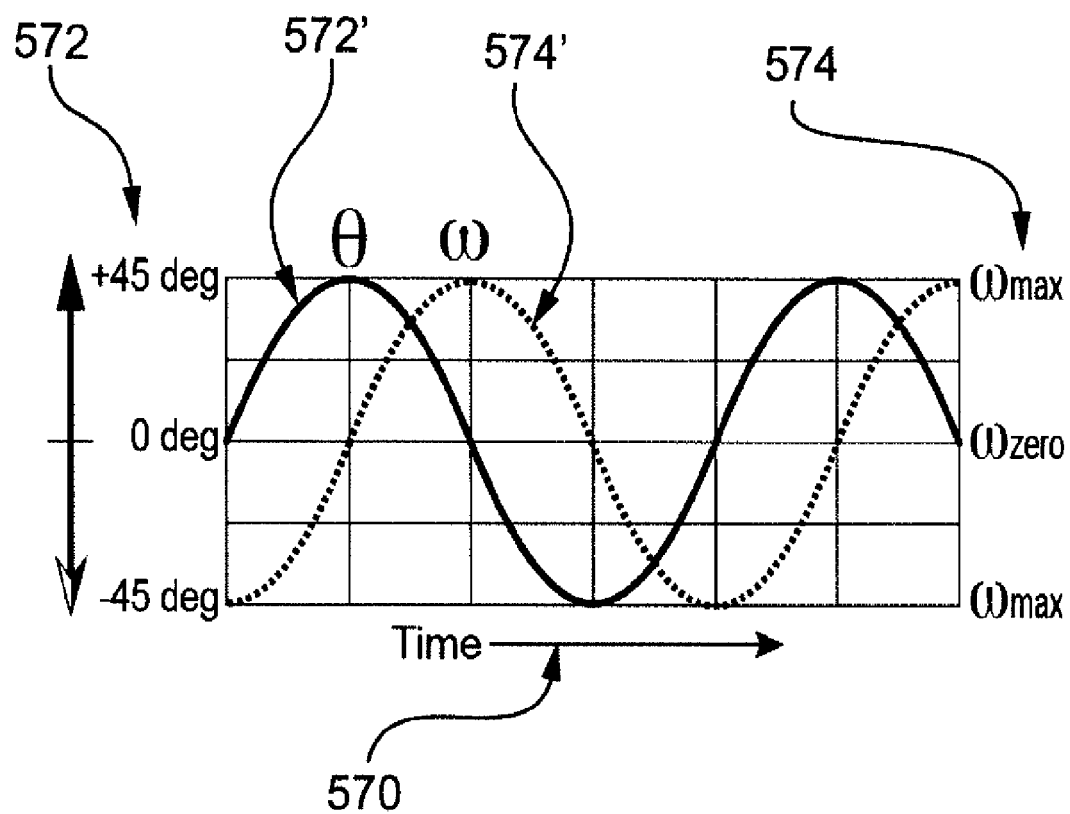

FIG. 5A-1 depicts one embodiment (and basic operation) of a steerable differential dissecting assembly 500 enabling differential dissection in any desired direction. Also disclosed is a steerable differential dissecting assembly 500, comprising a differential dissecting member 110 oscillatible about a substantially transverse axis of member rotational oscillation 112, a drive means 160 for driving the differential dissecting member 110 in oscillations about substantially transverse axis of member rotational oscillation 112, and a tissue engaging surface 120 forming the distal-most portion of the steerable differential dissecting assembly 500. The differential dissecting member 110 has an amplitude of oscillation 538 of the differential dissecting member 110, a magnitude of travel 536 of the drive means 160, a leftward swing 537' of the differential dissecting member 110, a leftward-driving input 537 driving the leftward swing 537', a rightward swing 539' of the differential dissecting member 110, a rightward-driving input 539 driving the rightward swing 539', a center of oscillation 538' of the differential dissecting member 110 that is substantially halfway between the leftward swing 537' and the rightward swing 539', and a direction of dissection 121 substantially aligned with the a center of oscillation 538' of the differential dissecting member 110.

Figures 2, 6A:
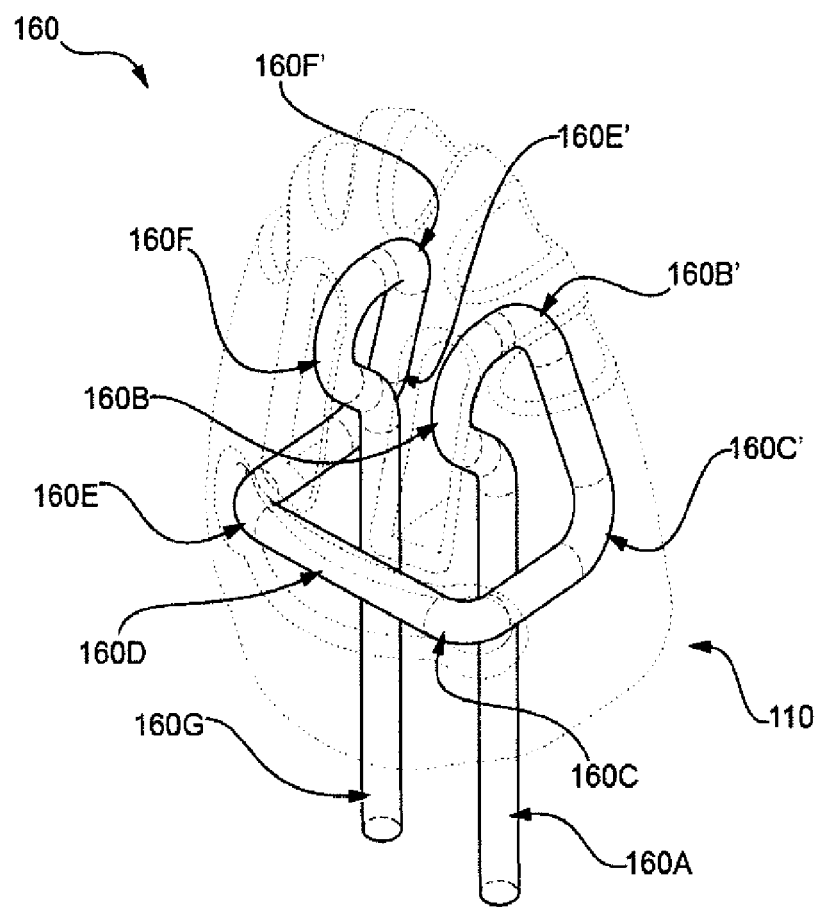

In operation, the steerable differential dissecting assembly 500 oscillates the differential dissecting member 110 via the a drive means 160, which can be a cable drive 160 as in FIG. 6A-1, or a oscillatory drive train as shown in FIGS. 3A and 4A. The amplitude of oscillation 538 of the differential dissecting member 110 is controlled by the magnitude of travel 536 of the drive means 160, and the leftward-driving input 537 and the rightward-driving input 539 control the left and right swings 537' and 539', respectively.

Still referring to FIG. 5A-1, the differential dissecting member 110 typically oscillates left and right to either side of the center of oscillation 538 about a substantially transverse axis of member rotational oscillation 112, driven by a cable loop 160, and presenting a tissue engaging surface 120 distally to the complex tissues to be dissected. In this view, the direction of rotation of the differential dissecting member 110 about the substantially transverse axis of member rotational oscillation 112 (and so the motion of the tissue engaging surface 120 against the complex tissue) depends on the balance of tension applied to the ends of cable loop 160. The authority (i.e., the surplus of force of the tissue engaging surface, relative to the force required to dissect the tissue) of the motion of the tissue engaging surface 120 against the complex tissue depends on the magnitude of the tension applied to the entire cable loop 160. The amplitude of the oscillation 538 about the center of oscillation 538' depends on the magnitude of travel 536 through which the cable loop 160 travels. The overall motion of the differential dissecting member 110 is thus a function of the motion of the cable loop 160, such that a leftward-driving input 537 (half-shaded bold arrows) results in a leftward swing 537' of the differential dissecting member 110, while a rightward-driving input 539 (solid black bold arrows) results in a rightward swing 539' of the differential dissecting member 110.

Continuing with FIG. 5A-1, the differential dissecting member 110 is depicted oscillating in a steady, symmetrical, sinusoidal fashion 45 degrees to either side of a center of oscillation 538 that points exactly distal, coincident with the longitudinal axis 398 of the differential dissecting instrument and directed toward the tissue to be dissected. The direction of dissection 121 in this case point forward, in that the complex tissue is dissected directly in front of the differential dissecting attachment.

Disclosed in FIG. 5A-2 is a schematic of the regular sinusoidal motion of the differential dissecting member 110 in FIG. 5A-1. Time 570 forms the x-axis, the y-axis is shown on the left-hand side as theta [θ], angular position 572 of the differential dissecting member 110, in degrees away from the center of oscillation 538', while the y-axis is shown on the right-hand side as omega [ω], rotational velocity 574 of the differential dissecting member 110. The rotational velocity 574 of the differential dissecting member 110 drops to zero as its angular position 572 reaches the extreme of 45 degrees, and the rotational velocity 574 of the differential dissecting member 110 reaches its maximum when the angular position 572 crosses zero degrees. This example of motion of the differential dissecting member 110, that is, regular sinusoidal oscillation about a center of oscillation 538' that is coincident with the longitudinal axis 398 of the differential dissecting attachment 100, so that the direction of dissection 121 is exactly distal, can be considered typical state of a differential dissecting attachment. That said, it is by no means a limiting case, as there is much to be gained by dynamically varying the rotational velocity 574, the angular position 572, or both.

Figures 1, 5B:
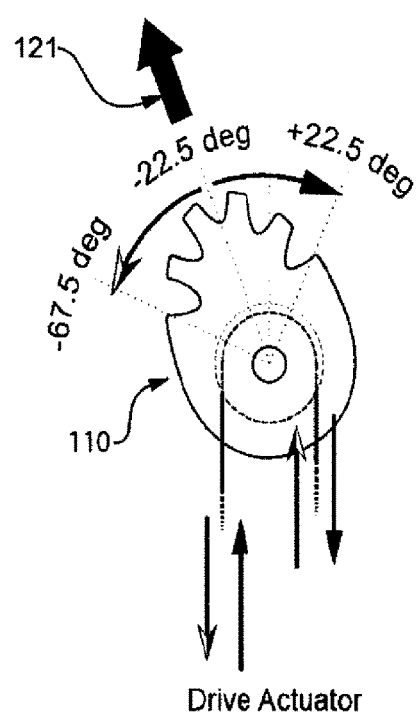
Figures 2, 5B:
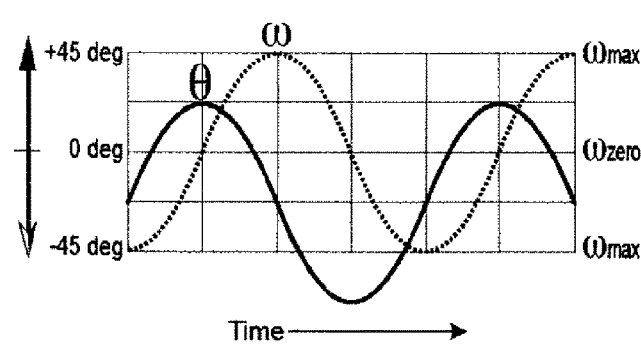

Referring to FIGS. 5B-1 and 5B-2, one may change the direction of dissection 121, in this example by offsetting the center of oscillation 538' (hereby −22.5 degrees, to the viewer's left) without changing the amplitude of oscillation 538; this is done by shifting the cables proximal on the left side and more distally on the right. Given that the differential dissecting member 110 now effectively points to the left, oscillation about the center of oscillation 538' drives dissection up and to the left. When the differential dissector 500 is thrust forward, resistance from the tissue to be dissected is reduced there as the tissues give way, and so the differential dissecting dissector 500 steers left. The direction of dissection 121 can be changed at will by controlling the motion of the drive means 160, which in this embodiment is the cable loop 160.

Referring to FIGS. 5B-1 and 5B-2, these figures depict a cable-driven, controllable differential dissecting member 110 oscillating in a steady, symmetrical, sinusoidal fashion about an offset center of oscillation 538' that points at a non-zero angle (here, 22.5 degrees to the viewer's left) from the longitudinal axis of the differential dissecting instrument. The direction of dissection 121 thus points to the left, and, as the differential dissecting member 110 oscillates about that leftward-leaning offset center of oscillation 538', and so the direction of dissection 121. Thus the tissue to be dissected gives way preferentially on the left, and the resistance of dissection decreases on the left, and the steerable differential dissecting assembly 500 tunnels to the left. In this way, the steerable differential dissecting assembly 500 can be directed to tunnel in any desired direction by controlling the offset.

Figures 1, 5D:
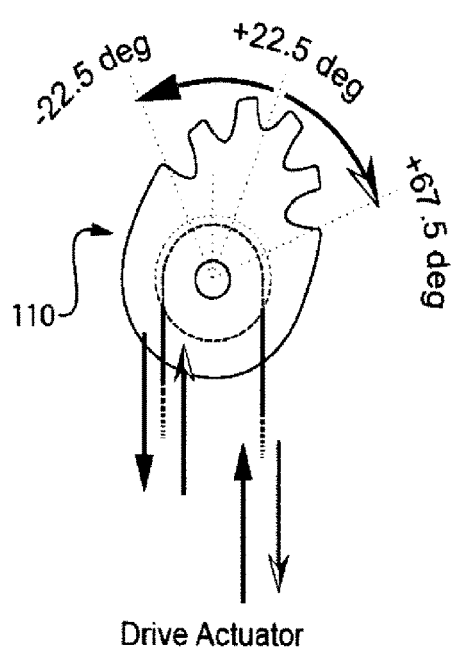
Figures 2, 5D:
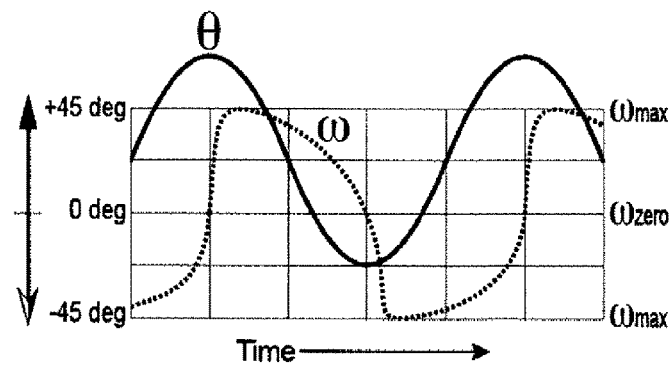

FIGS. 5C-1 and 5C-2 depict a cable-driven, controllable differential dissecting member oscillating in a symmetrical fashion, but with a varying angular velocity profile, about a center of oscillation 538' that points exactly forward about the longitudinal axis 398 of the differential dissecting instrument. The varying angular velocity profile generates off-axis forces against the tissue to be dissected, thus driving the direction of dissection 121 off-axis, and the steerable differential dissecting assembly 500 dissects preferentially in that direction. FIGS. 5D-1 and 5D-2 depict a cable-driven, controllable differential dissecting member 110 oscillating in a steady, symmetrical, sinusoidal fashion, but with a varying angular velocity profile, about a center of oscillation 538' that points at a non-zero angle from the longitudinal axis 398 of the differential dissecting instrument. The combination also generates asymmetrical dissection, driving a change in the direction of dissection 121, allowing the steerable differential dissecting assembly 500 to dissect in a direction chosen by the surgeon.

Figures 1, 5E:
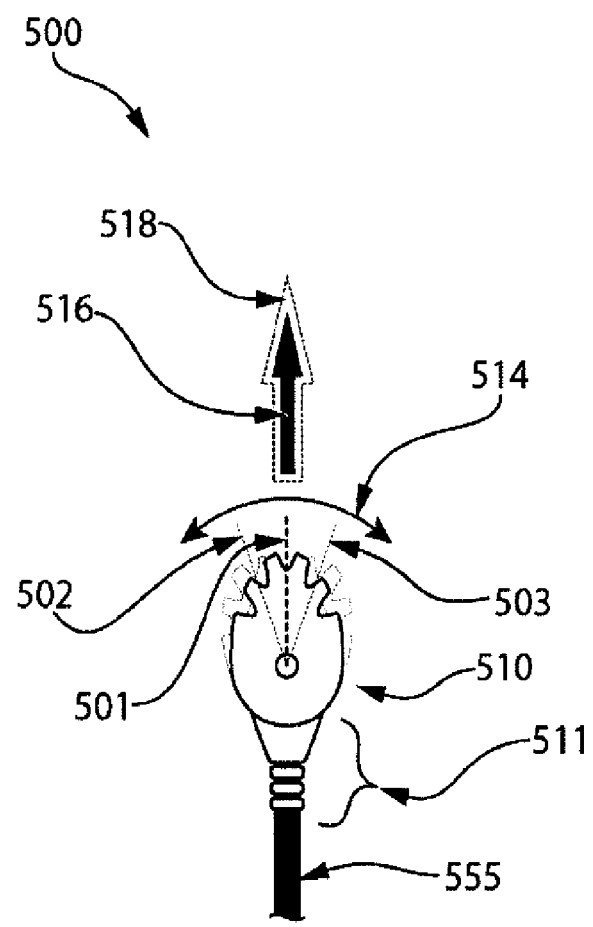
Figures 2, 5E:
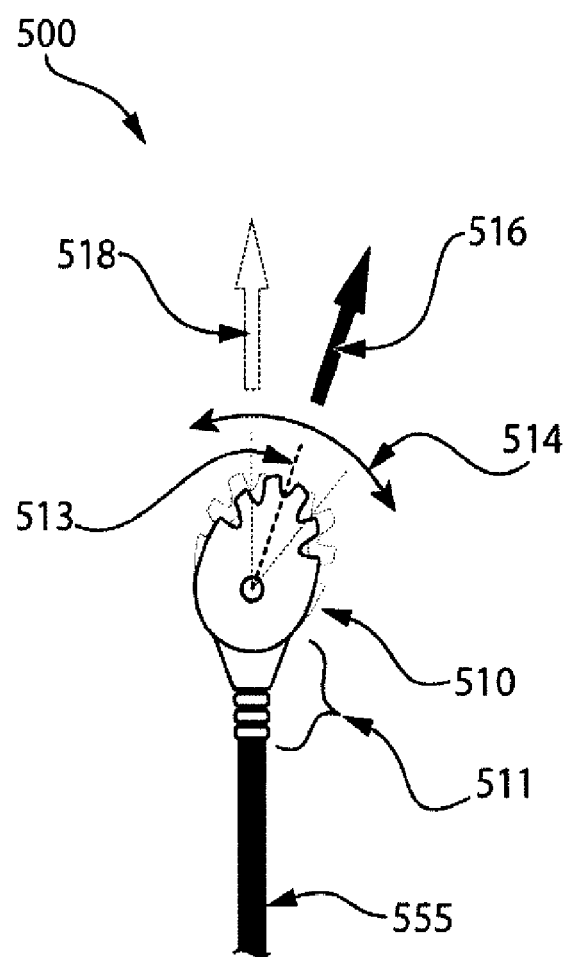
Figures 3, 5E:
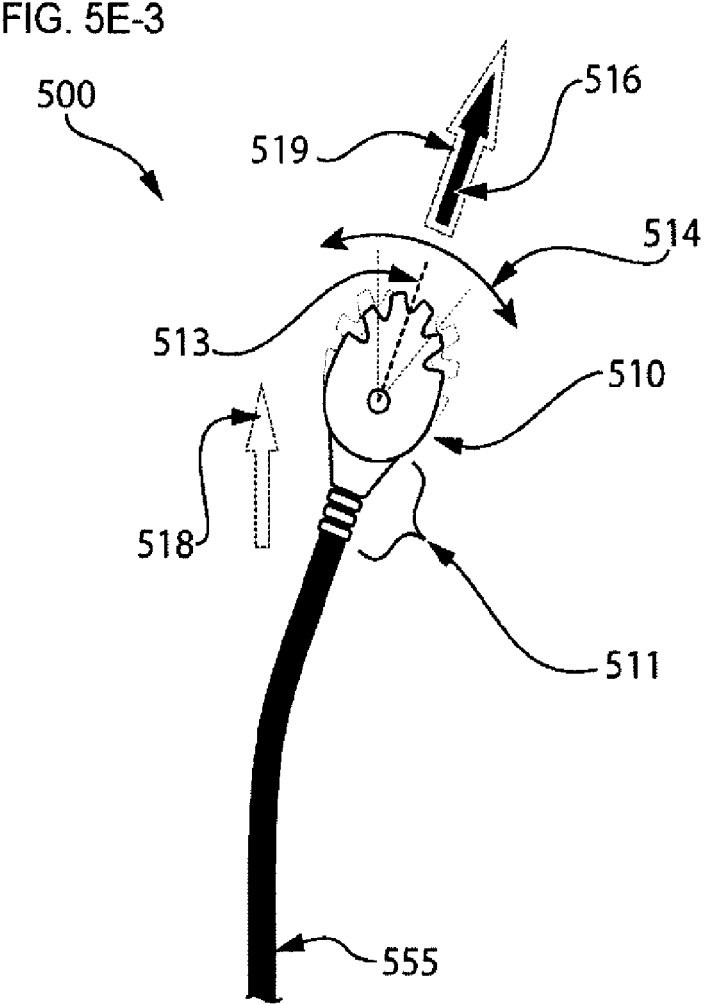

FIGS. 5E-1 through 5E-3 show a controllable differential dissecting dissector 500 located at the distal end of an endoscope, oscillating about a center of oscillation 501, creating a direction of dissection, and dissection in that direction, and showing arbitrary control of the direction of dissection thus permitting tunneling in arbitrary directions within complex tissues. FIG. 5E-1 shows the steerable differential dissecting assembly 500, comprising a differential dissecting member 510 fixed to oscillate on the distal-most portion 511 of a flexible instrument shaft 555, the oscillation possessing a center of oscillation 501, a first extent of oscillation 502 and a second extent of oscillation 503, and an amplitude of oscillation 514 defined by the angle between the first extent of oscillation 502 and a second extent of oscillation 503. The steerable differential dissecting assembly 500 further comprises a longitudinal axis 518 and a direction of dissection 516. The differential dissecting member 510 is not unlike the others disclosed in this document, possessing a tissue engaging surface, a substantially transverse axis of member rotational oscillation, and the like. Of interest here is the control of the direction of dissection 516 by modulating the properties of oscillation of the differential dissecting member 510, chiefly the offset of the center of oscillation 501, and secondly, by varying the rotational velocity of the differential dissecting member 510. The direction of dissection 516 is defined as the center of the narrow region of tissue that experiences a sufficient differential dissection effect so that a complex tissue there differentiates into preserved firm or organized tissue and disrupted soft, less-well organized tissue.

In normal operation, the direction of dissection 516 is coincident with the center of oscillation 501. As the differential dissecting member 510 oscillates, it typically oscillates sinusoidally about a center, usually halfway between the first extent of oscillation 502 and a second extent of oscillation 503; we define that halfway point as the center of oscillation 501. The oscillations of a differential dissecting member 510 are determined in a cable-driven device as disclosed in FIGS. 3A and 5A-1 to 5D-2 by the magnitude of the change in tension (and so, position) over time; a oscillatory drive train as disclosed in FIGS. 3A, 4A can vary motor speed. Thus, the direction of dissection 121 (or 516) is controllable at the discretion of the surgeon.

Referring now to FIGS. 6A-1 through 6B-5, to ensure improved performance and safety for a differential dissecting instrument, we disclose below, and first in FIG. 6A-1, another embodiment 600 of a differential dissecting member 110. This differential dissecting member 110 is captured by, and driven to oscillate by, a continuous, circuitous loop 160 of fine wire rope or cable passing through a series of fenestrations (passages) through the body 111 of the differential dissecting member 110 and proximally away to a drive mechanism. The continuous, circuitous loop 160 is made up of portions 160A-160G of a fine wire rope or cable. The circuitous route of the loop through and around the body 111 of the differential dissecting member 110 forms a "lark's head" or "cow-hitch" knot, a topologically constrained path that captures the differential dissecting member 110, preventing its loss.

Describing the elements of this embodiment in detail, the differential dissecting member 110 has a longitudinal axis 398 with a first, proximal end 397 substantially directed toward a drive mechanism on, within, or associated with a handle or surgical robot, and a second, distal end 396, substantially directed distally toward a tissue to be dissected. The differential dissecting member 110 is rotatable about a substantially transverse axis of member rotational oscillation 112 which is perpendicular to the longitudinal axis 398 and located near the longitudinal axis 398's second, distal end 396. The differential dissecting member 110 further has a roughly wedge-like body 111, which is substantially aligned with the longitudinal axis 398, and a tissue-engaging surface 120 substantially directed distally toward the tissue to be dissected and forming the somewhat thinner tip of the wedge-like body. The body further possesses a first face side 691 of the wedge-like body 111 and a second, back side 692 of the wedge-like body 111.

The body 111 of the differential dissecting member 110 further comprises a series of short, shallow surface troughs and through-body-holes (passages) which are adapted to accept, capture, and allow passage of a continuous loop of fine wire rope or cable that holds the differential dissecting member 110 to the rest of the surgical instrument. The first, face side 691 has a mouth-like trough 166 and two eye-like troughs 162 and 164. The second, back side 692 has two ear-like troughs 162' and 164'. The mouth-like trough 166 further comprises two passages 161C and 161D which pass completely through the body 111 of the differential dissecting member 110. The eye-like trough 162 has a passage 161B passing through to the second, back side of the differential dissecting member 110, and a longitudinally-oriented passage 161A that travels out the bottom of the differential dissecting member 110. The eye-like trough 164 has a passage 161E passing through to the second, back side of the differential dissecting member 110, and a longitudinally-oriented passage 161F that travels out the bottom of the differential dissecting member 110. Viewing also FIGS. 6B-1 (a direct view of the first, face side 691 of the differential dissecting member 110) and 6B-2 (a direct view of the second, back side 692 of the differential dissecting member 110), we see that there on the second, back side 692 are two more troughs: ear-like trough 164', further comprising the passage 161E and the passage 161D, and ear-like trough 162', further comprising the passage 161B and the passage 161C.

Still referring to FIGS. 6A-1, 6B-1, and 6B-2, review now the circuitous path of the cable loop 160 depicted clearly in FIG. 6A-2. Following the cable loop 160 around through the passages, we see that the cable loop section 160A first passes up distally through passage 161F into the bottom of the eye-like trough 164 in the first, face side 691 of differential dissecting member 110. The cable loop 160 then travels from there up distally through the eye-like trough 164 as loop section 160B and passes from the first, face side 691 through passage 161E, emerging as loop section 160B' into the ear-like trough 164' on the second, back side 692 of the differential dissecting member 110. The cable loop 160 then turns and travels proximally down through that trough 164', and, as loop section 160C', passes through passage 161D, emerging as loop section 160C into the mouth-like trough 166 in the first, face side of differential dissecting member 110. The loop then passes as loop section 166D in the mouth-like trough 166, traversing the face of the first, face side 691.

The inventors of the subject matter disclosed in this application have found it advantageous to further design the mouth-like trough 166 to "bite" or "pinch" the cable loop 160. This feature is most clearly observed in FIG. 6B-5, the profile view of the embodiment 600 of the differential dissecting member 110. By providing the body 111 of the differential dissecting member 110 with the mouth-like trough 166, farthest from the harsh cyclic loads near the ends of the cable loop 160, the differential dissecting member 110 can thus pinch the fine cable or wire loop 160, securing it cleat-like in the mouth-like trough 166 where the stresses that would tend to dislodge it are the lowest. This will help ensure that the entire cable loop 160 cannot reptate (i.e., slide) through the circuitous route formed by the series of passages and troughs formed in the body of the differential dissecting member 110. We can in this view clearly observe the substantially straight, wedge-like form of the body 111 of the differential dissecting member 110 that helps divide and pre-tension the complex tissue to be dissected. Also visible in this view is the length of the passage 161D traveling from the eye-like trough 164 set deeply into the first, face side 691, through to the ear-like trough 164' set into the second, back side 692 of the body 111 of the differential dissecting member 110. Further visible is the passage 161D connecting the mouth-like trough 166 in the first, face side 691 and the eye-like trough 164' set in the second, back side 692 of the body 111 of the differential dissecting member 110 comprising this preferred embodiment 600. The body 111 of the differential dissecting member 110 further comprises stabilizers 999, that help secure the differential dissecting member 110 onto an axle whose axis is coincident with the substantially transverse axis of member rotational oscillation 112, the stabilizers 999 further possessing a shape allowing clearance for the cable loop section 160A.

Continuing with the circuitous loop (and referring back to FIGS. 6A-1, 6B-1, and 6B-2), the path of the circuitous loop can be traced substantially symmetrically through the remaining passages. The cable loop 160 completes its traverse of the first, face side 691 in the mouth-like trough 166, then passing as loop section 160E away from the first, face side 691 through passage 161C to emerge on the second, back side 692 as loop section 161E' into the proximal-most end of ear-like trough 162'. From there the cable loop 160 circuits distally along ear-like trough 162' until it reaches passage 161B as loop section 160F', where it passes through to emerge on the first, face side 691 as loop section 160F in the eye-like trough 162. The cable loop 160 then leaves the first, face side 691 for last time and descends proximally down, following the eye-like trough 162 until it passes into and through passage 161A, until it emerges as loop section 160G, and heads proximally toward the first, proximal end 397 of longitudinal axis 398.

Referring again to FIG. 6A-1, note that this embodiment 600 of a differential dissecting member 110 further includes developing opposed tensile forces 137 and 139 on the cable loop sections 160G and 160A, respectively. Note further that when tensile force 137 is greater than tensile force 139, so that an imbalance is present. This force imbalance drives the differential dissecting member 110 to rotate about the substantially transverse axis of member rotational oscillation 112 in the direction of arrow 136. Conversely, if the tensile force 139 becomes greater than the tensile force 137, then the differential dissecting member 110 rotates about axis 112 in the direction of arrow 138. The tensile forces on the ends 160G and 160A of the cable loop 160 are provided remotely by a drive mechanism located proximal to this embodiment 600 of the differential dissecting member 100. The useful cable oscillation frequencies for effective differential dissection are between 10 Hz and 1 KHz, with a preferred range between 50 Hz and 500 Hz.

Reviewing now FIG. 6A-2 one last time, it can be seen in this view (where the differential dissecting member 110 is transparent to expose the complete circuitous route of the cable loop 160) that nowhere does the cable loop 160 come into contact with itself, nor does the cable loop 160 bend at a radius small enough to kink, reducing the chances of the cable loop 160 damaging itself under load. The cable loop 160 passes completely through six holes in the body 111 of the differential dissecting member 110, increasing greatly the odds of the complete capture of the differential dissecting member 110, helping to prevent its loss during surgery. The five troughs are so designed as to allow the cable to wrap around and through the body 111 of the differential dissecting member 110 as deep into (and preferably below) the outer surfaces of the differential dissecting member 110.

Referring now to FIGS. 6B-1, 6B-2, 6B-4, and 6B-5, a further feature of the design of this embodiment 600 of a differential dissecting member 110 is an cylindrical axle well 199. The cylindrical axle well 199 preferably faces directly proximally, and has a transverse long axis formed by the transverse axis of member rotational oscillation 112, concentric with a bearing cavity 114 (see FIG. 3B). Designed to accept an axle, the axle well 199 can be seen in FIGS. 6B-1 and 6B-2 that this embodiment 600 of a differential dissecting member 110 requires the proximally directed tensile forces 137 and 139 to remain seated upon an axle. Further, we can see that the design of the differential dissecting member 110 further incorporates nearby stabilizers 999, the better to prevent dislodgement of the differential dissecting member 110 from atop the distal end 396 of the differential dissecting instrument. The shape of the stabilizers 999 further admit sweeping at large angles by the cable loop 160 while it is under tension, so that the stabilizers 999 cannot interfere with the smooth action of the cable loop 160.

Figures 1, 6B:
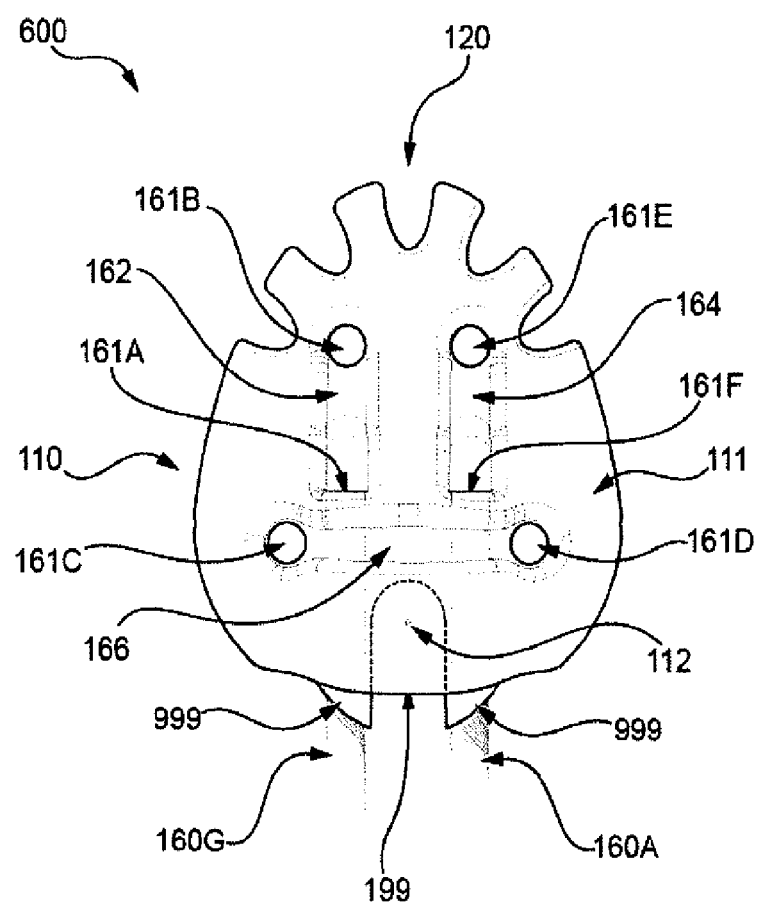
Figures 2, 6B:
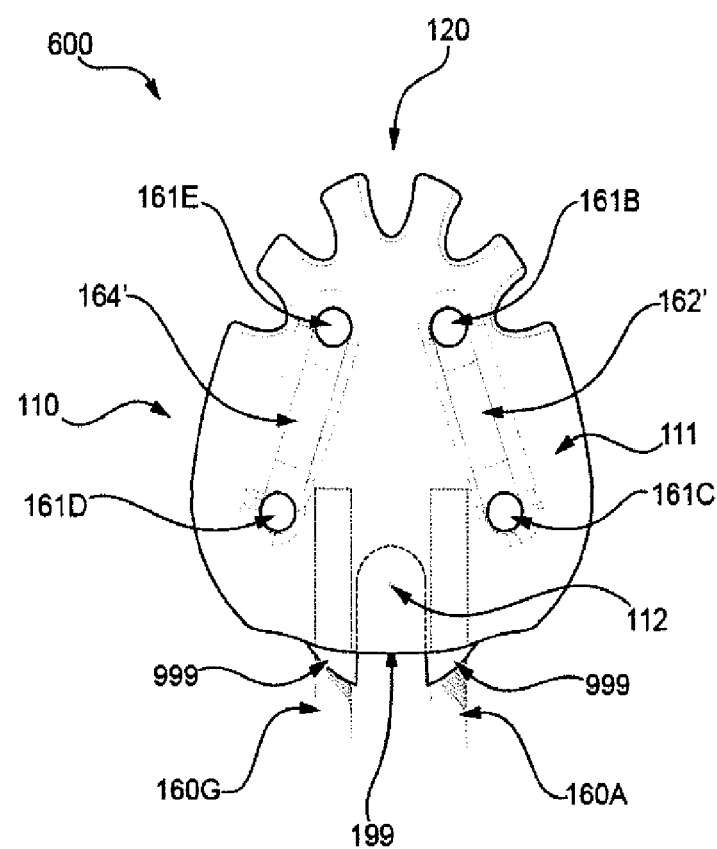
Figures 4, 6B:
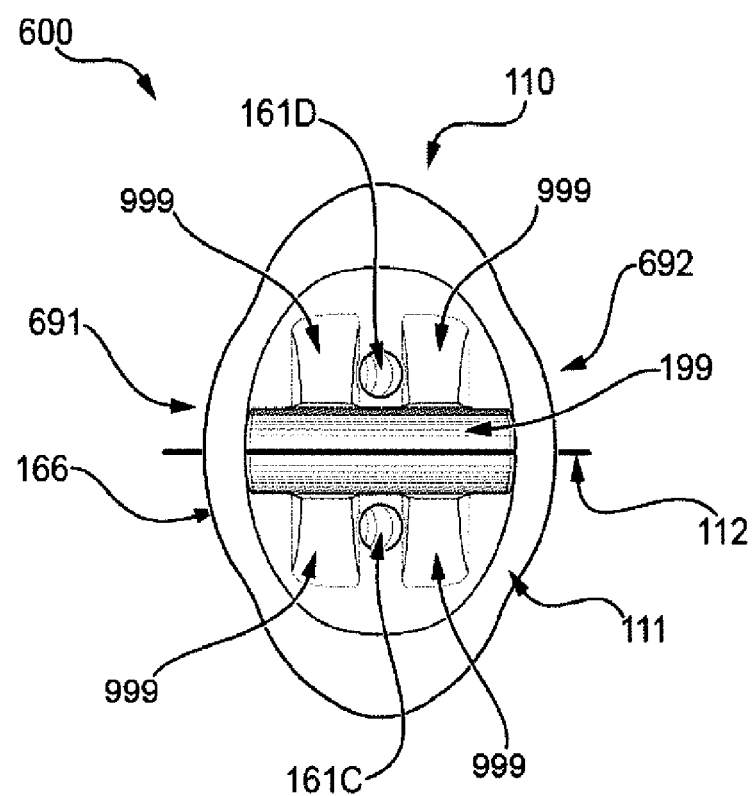
Figures 5, 6B:
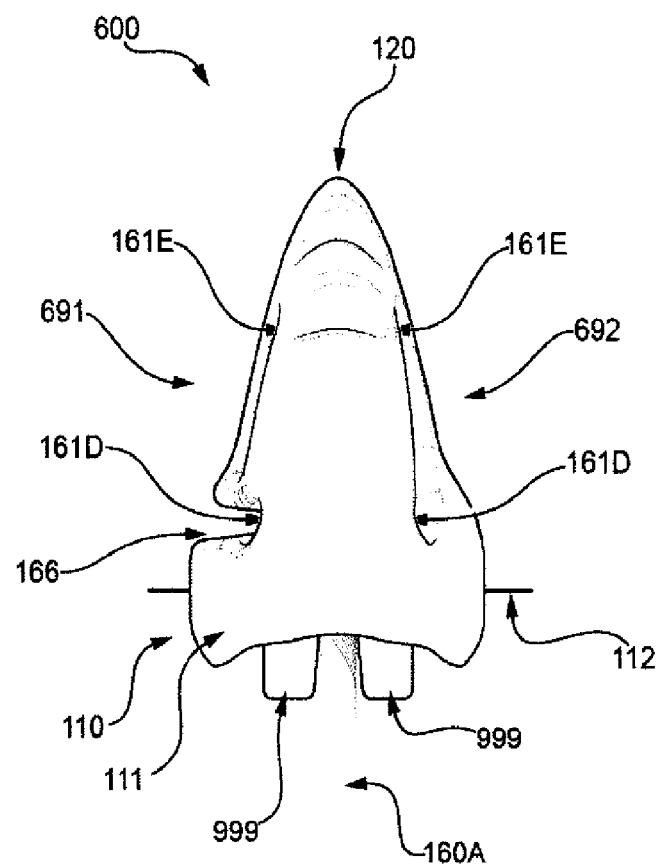

Lastly, the short lengths of the passages can clearly be seen in FIG. 6B-3, which depicts a top view looking back proximally the embodiment 600. The differential dissecting member 110 possesses a body 111, a substantially transverse axis of member rotational oscillation 112, a tissue engaging surface 120 (in this view, directed at the viewer), a first, face side 691, a second, back side 692, and a plurality of troughs and passages formed in the body 111 of the differential dissecting member 110. One can see that passage 161D enters through the ear-like trough 164' in the second, back side 692 and emerges in the mouth-like trough 166 in the first, face side 691. The passage 161E enters through the ear-like trough 164' in the second, back side 692 and emerges in the eye-like trough 164 in the first, face side 691. Passage 161B enters through the ear-like trough 162' in the second, back side 692 and emerges in the eye-like trough 162 in the first, face side 691. Passage 161C enters through the ear-like trough 162' in the second, back side 692 and emerges in the mouth-like trough 166 in the first, face side 691. At no time do the passages require the cable loop 160 (see FIG. 6A-2) to bind upon itself, so reducing the chances of cable wear and tear.

It is often useful to be able to dissect in a straight line, directly forward. In the embodiment 600 shown again in FIGS. 6A-1 through 6B-5, a substantially straight-bodied differential dissecting member 110 for dissecting a complex tissue is disclosed. The differential dissecting member 110 comprises a body 111 having a longitudinal axis 398, with a first, proximal end 397 and a second, distal end, 396. The longitudinal axis 398 is aligned with the differential dissecting member 110 when the member 110 is centered in its travel sweep along planar motion 392. The wedge-shape of the body 111 of the differential dissecting member 110 is designed to dissect directly in front of the differential dissecting handheld open surgical instrument, differential dissecting laparoscopic instrument, or differential dissecting surgical robot arm to which it is attached to enable differential dissection. So, again, in this embodiment 600, the mass of the body 111 of the differential dissecting member 110 is arranged in a substantially straight fashion along the longitudinal axis 398, and the differential dissection effect occurs in a region substantially directly along the axis of the differential dissecting member 110, that is, tissues are separated by the tissue engaging surface 120 in a region directly distal to the tip of the device. A straight instrument serves well enough for many procedures most of the time.

Figures 1, 6C:
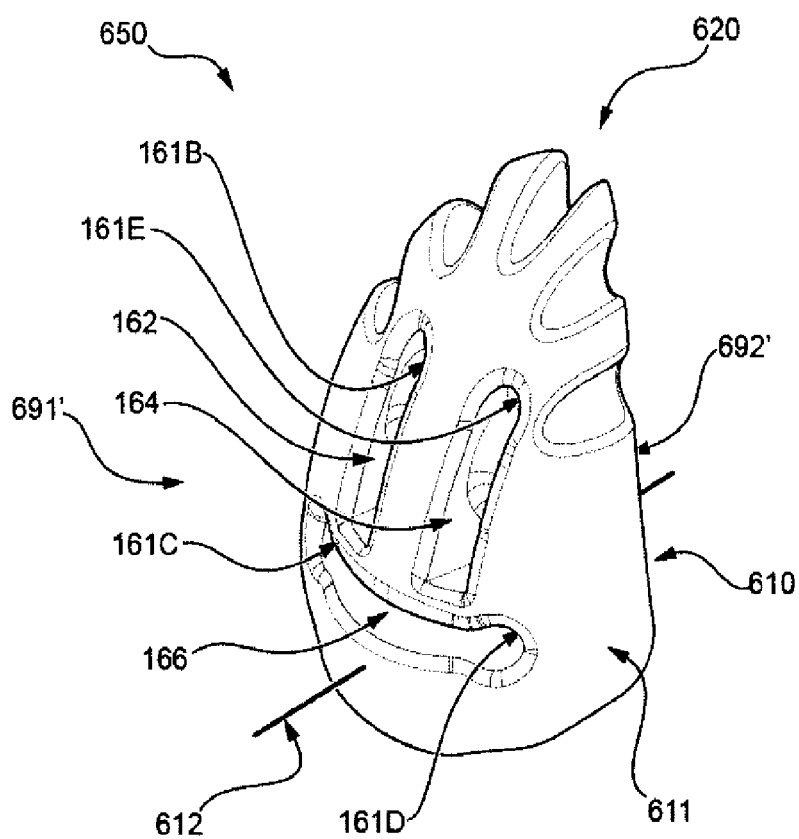
Figures 3, 6C:
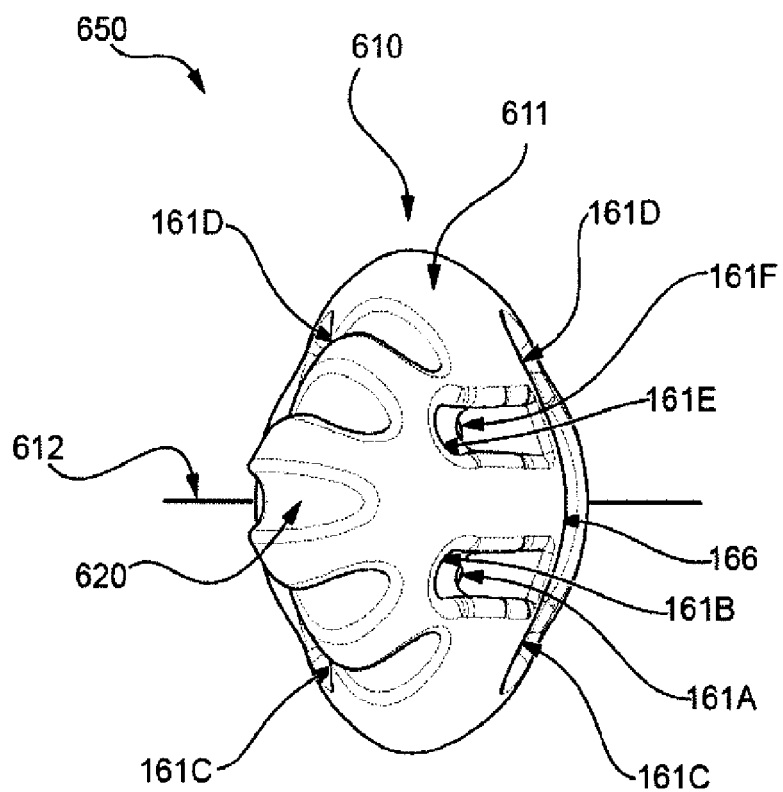

Surgeons, however, often require access to target structures hidden behind other delicate, critical structures that must not be damaged. This kind of surgery is tedious and taxing on all involved. Surgeons are also often called upon to reach or expose critical structures that are found in tight spaces where straight instruments will simply not fit. In an embodiment related to that we disclosed above, we here further teach a curved oscillating differential dissecting member. FIGS. 6C-1 through 6C-3 depict oblique, side, and end views of another embodiment 650 of a cable-retained differential dissecting member 610 with a distinctly curved profile. The curved differential dissecting member 610 comprises a body 611 having a first end and a second end, and with a central axis 398 from the first end to the second end. In this embodiment, however, the tissue engaging surface 620 of the differential dissecting member 610 is arranged in a substantially curved form, away and to one side of the longitudinal axis 398, and out of the plane of oscillation 392 of the member 610, such that the alternating series of at least one valley and at least one projection comprising a tissue engaging surface 620 is arrayed entirely on one side of the plane of oscillation 392, so that they never cross it during oscillation of the curved differential dissecting member. This causes the differential dissection effect to occur in a region substantially to one side of the axis of the device, permitting a surgeon to perform blunt dissection around and behind otherwise occluding tissues.

The previous embodiments of differential dissecting devices have mostly relied on axles, bushings, roller bearings, and the like for creating and supporting the substantially transverse axis of member rotational oscillation of the disclosed differential dissecting members. Axles and roller bearings can clog, jam, or otherwise develop issues that could interfere with a differential dissecting member oscillating at a few hundred Hertz, under severe and variable loads, for a million cycles or more. Furthermore, it is desirable to reduce the number and complexity of the parts in the device to increase safety and reduce cost. And, reducing relative motion between what parts remain can reduce wear and tear, reduce radiated noise, and increase the performance of the device.

Figure 7:
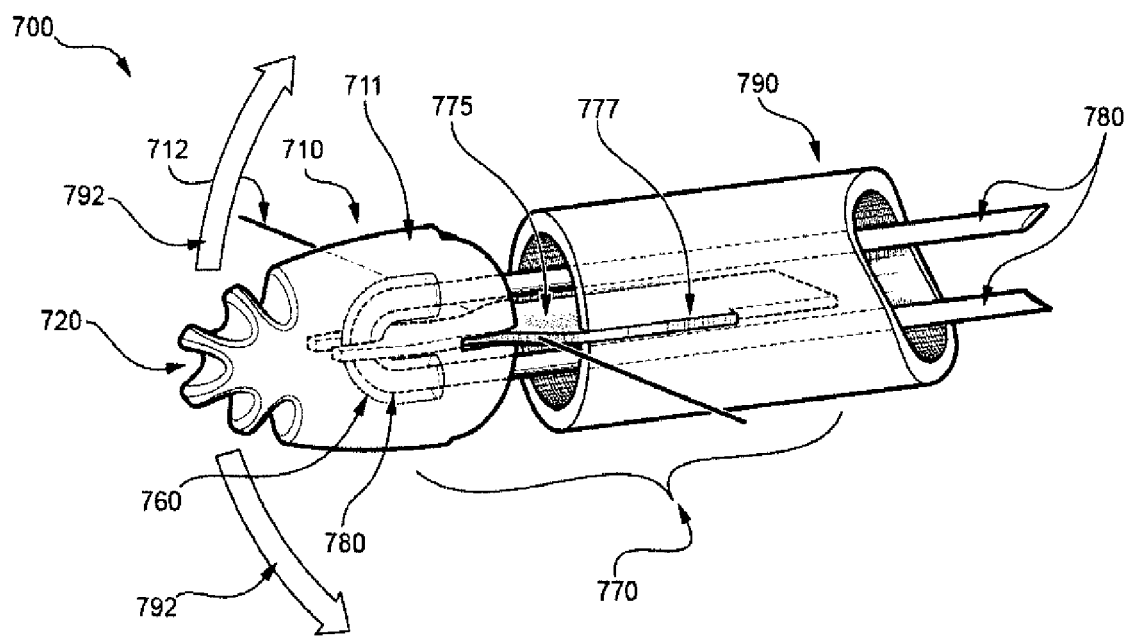
FIG. 7 shows an oblique view of a cable-driven differential dissecting member, where the axis of rotation of the differential dissecting member is formed by an elastic planar member, such as a leaf spring, the end of which the differential dissecting member is operably mounted.

Disclosed in FIG. 7 is an alternative means for supporting a differential dissecting member 710 under these conditions. FIG. 7 depicts an oblique view of an embodiment 700 of a cable-driven differential dissecting assembly comprising an elongate shaft 790 through which pass cables 780 which are attached to a differential dissecting member 710 disposed distal-most and near the shaft 790. The differential dissecting member 710 also possesses a body 711, a tissue engaging surface 720, a substantially transverse axis of member rotational oscillation 712, and a desired plane of oscillatory motion 792 oriented substantially perpendicular to the substantially transverse axis of member rotational oscillation 712. The differential dissecting member 710 further comprises an internal cavity 760 admitting and capturing at least a portion of the drive cable 780. This embodiment 700 also comprises an elastic planar member 775 oriented substantially parallel to the elongate shaft 790 and with its planar form oriented substantially perpendicular to the desired plane of oscillatory motion 792 of the differential dissecting member 710. The elastic planar member 775 may be made of any convenient material that is stiff within its own plane, but will deflect out-of-plane (i.e., bend) when subject to out-of-plane loading. The elongate shaft 790 may also possess a attachment means 777 designed to accept and anchor a portion of the elastic planar member 775. The internal cavity 760 of the differential dissecting member 710 may also accept, bond with, and retain and thereby be disposed upon the distal-most portion of the elastic planar member 775. Thus the differential dissecting member 710 resides on the elastic planar member 775, which itself resides at the distal-most portion of the elongate shaft 790.

It is important to note that in this embodiment 700, the substantially transverse axis of member rotational oscillation 712 is parallel to and coincident with the plane defined by the elastic planar member 775; that is, the substantially transverse axis of member rotational oscillation 712 ideally passes through the middle of the thickness of the elastic planar member 775. There is no axle, roller bearing, or other wheel-like feature per se that enables the rotation in the desired plane of oscillatory motion 792. Also, it is important to observe from FIG. 7 that the cables depicted pass on either side of the elastic planar member 775.

In operation, providing the oscillating cable tension imbalance as disclosed above at least in FIG. 6A-1, the differential dissecting member 710 residing on the elastic planar member 775 is subject to out-of-plane loading, so that the differential dissecting member 710 residing on the elastic planar member 775 deflects (in the desired plane of oscillatory motion 792) to that side of the elastic planar member 775 subject to the greater tension. Thus, if the cables 780 are subject to an oscillating tension imbalance at a given frequency, the differential dissecting member 710 and the elastic planar member 775 will oscillate within the desired plane of oscillatory motion 792 at the same frequency. Given that the natural frequency of oscillation of a cantilevered beam is proportional to the square root of the flexural stiffness of the beam divided by the mass of the beam, and given that the energy required to oscillate a beam is minimized (and amplitude is maximized) at the natural frequency of oscillation of that beam, it may be desirable to design the flexural stiffness, mass, length and other properties of the differential dissecting member 710 and elastic planar member 775 to operate at the desired frequencies that are preferable for performing safe, differential dissection. Thus, the embodiment 700 of the differential dissector can be tuned to minimize the energy required to operate the device, to maximize the amplitude of the oscillation of the differential dissecting member 710 within the desired plane of oscillatory motion 792, or a combination thereof, including the accommodations and requirements for particular surgical procedures.

One normally skilled in the art will appreciate that many variations and combinations of the devices and components herein are possible without violating the spirit of the invention.

We claim:

1. A differential dissecting member for differentially dissecting complex tissue comprising:
   a body having a longitudinal axis, a distal end configured to engage a tissue, and a proximal end directed toward a drive mechanism, wherein the proximal end of the body is configured to operatively engage an axle associated with the body; and
   a looped oscillating drive cable operatively associated with the drive mechanism and affixing the body to the drive mechanism via a circuitous path, wherein the circuitous path comprises at least one topologically constrained tortuous loop through the body, and wherein the looped oscillating drive cable is captured in at least one passage through which the looped oscillating drive cable passes, such that proximal movement of one end of the looped oscillating drive cable and distal movement of another end of the looped oscillating drive cable produces a rotation, and wherein the looped oscillating drive cable is configured to drive the body to high speed oscillations.

2. The differential dissecting member as in claim 1, where the circuitous path comprises a plurality of troughs in the body, and wherein the looped oscillating drive cable is held in place in at least a portion of at least one trough.

3. The differential dissecting member as in claim 1, wherein the circuitous path comprises penetrating a fenestration of the body.

4. The differential dissecting member as in claim 1, wherein the circuitous path comprises penetrating a plurality of fenestrations of the body.

5. The differential dissecting member as in claim 1, where the body comprises six fenestrations and the circuitous path of the looped oscillating drive cable is topologically constrained by penetrating the six fenestrations.

6. The differential dissecting member as in claim 1, wherein at least one portion of the looped oscillating drive cable is subject to tension directed substantially proximally, and where said tension possesses a magnitude, and where the magnitude of said tension holds the body operatively on the axle.

7. The differential dissecting member as in claim 2, wherein the at least a portion of the at least one trough holding the looped oscillating drive cable is configured as a cleat to pinch the looped oscillating drive cable therein, preventing reptation or sliding of the looped oscillating drive cable therethrough during the high speed oscillations.

8. The differential dissecting member as in claim 6, wherein the magnitude of said substantially proximally directed tension is further modulated by the drive mechanism.

9. The differential dissecting member as in claim 1, wherein the body is wedge-shaped, with the distal end being narrower and the proximal end being wider.

10. The differential dissecting member as in claim 1, wherein the looped oscillating drive cable operates at a frequency between ten Hertz (10 Hz) and one KiloHertz (1 KHz).

11. The differential dissecting member as in claim 1, wherein the looped oscillating drive cable operates at a frequency between fifty Hertz (50 Hz) and five hundred Hertz (500 Hz).

* * * * *